United States Patent
Moffat et al.

(10) Patent No.: US 8,106,091 B2
(45) Date of Patent: Jan. 31, 2012

(54) INHIBITORS OF IKK-BETA SERINE-THREONINE PROTEIN KINASE

(75) Inventors: David Charles Festus Moffat, Abingdon (GB); Stephen John Davies, Abingdon (GB); Michael Hugh Charlton, Abingdon (GB); Simon Christopher Hirst, Nottingham (GB); Stuart Thomas Onions, Nottingham (GB); Jonathon Gareth Williams, Nottingham (GB)

(73) Assignee: Chroma Therapeutics Ltd. (GB)

( * ) Notice: Subject to any disclaimer, the term of this patent is extended or adjusted under 35 U.S.C. 154(b) by 330 days.

(21) Appl. No.: 12/447,271

(22) PCT Filed: Oct. 29, 2007

(86) PCT No.: PCT/GB2007/004117
§ 371 (c)(1),
(2), (4) Date: Sep. 24, 2009

(87) PCT Pub. No.: WO2008/053185
PCT Pub. Date: May 8, 2008

(65) Prior Publication Data
US 2010/0069473 A1  Mar. 18, 2010

(30) Foreign Application Priority Data

Nov. 1, 2006 (GB) .................................. 0621720.2
Aug. 9, 2007 (GB) .................................. 0715469.3

(51) Int. Cl.
*A61K 31/381* (2006.01)
*C07D 333/36* (2006.01)
(52) U.S. Cl. ......................................... 514/447; 549/69
(58) Field of Classification Search .................. 514/447; 549/69
See application file for complete search history.

(56) References Cited

FOREIGN PATENT DOCUMENTS
WO     03/010158 A   2/2003
WO   2004/063186 A   7/2004

OTHER PUBLICATIONS

International Search Report dated Feb. 12, 2008.

*Primary Examiner* — Taofiq A Solola
(74) *Attorney, Agent, or Firm* — Banner & Witcoff, Ltd.

(57) ABSTRACT

Compounds of formula (IA) or (IB) are inhibitors of IkB kinase (IKK) activity, and are useful in the treatment of autoimmune and inflammatory diseases:

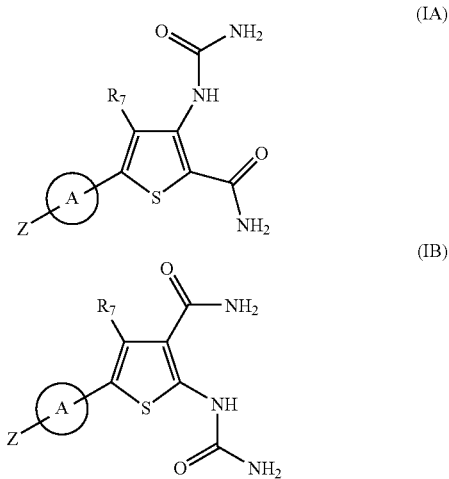

wherein $R_7$ is hydrogen or optionally substituted ($C_1$-$C_6$) alkyl; ring A is an optionally substituted aryl or heteroaryl ring of 5-13 ring atoms; Z is a radical of formula R-$L^1$-$Y^1$—$(CH_2)_z$—, wherein: z is 0 or 1; R is a radical of formula (X) or (Y)

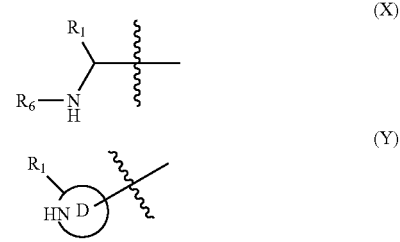

$R_1$ is a carboxylic acid group (—COOH), or an ester group which is hydrolysable by one or more intracellular esterase enzymes to a carboxylic acid group; $R_6$ is hydrogen, or optionally substituted $C_1$-$C_6$ alkyl, $C_3$-$C_7$ cycloalkyl, aryl or heteroaryl or —(C=O)$R_3$, —(C=O)O$R_3$, or —(C=O)N$R_3$ wherein $R_3$ is hydrogen or optionally substituted ($C_1$-$C_6$) alkyl; $Y^1$ is a bond, —(C=O)—, —S($O_2$)—, —C(=O)O—, —OC(=O)—, —(C=O)N$R_3$—, —N$R_3$(C=O)—, —S($O_2$)N$R_3$—, —N$R_3$S($O_2$)—, or —N$R_3$(C=O)N$R_4$—, wherein $R_3$ and $R_4$ are independently hydrogen or optionally substituted ($C_1$-$C_6$)alkyl, $L^1$ is a divalent linker radical of formula -(Alk$^1$)$_m$(Q)$_n$(Alk$^2$)$_p$- wherein m, n, p, Q, Alk$^1$ and Alk$^2$ are as defined in the claims.

15 Claims, No Drawings

INHIBITORS OF IKK-BETA SERINE-THREONINE PROTEIN KINASE

CROSS REFERENCE TO RELATED APPLICATIONS

This application is a National Stage application of co-pending PCT application PCT/GB2007/004117 filed Oct. 29, 2007, which claims the benefit of Great Britain application number 0621720.2 filed Nov. 1, 2006 and Great Britain application number 0715469.3 filed Aug. 9, 2007. These applications are incorporated herein by reference in their entireties.

This invention relates to thiophene carboxamides characterised by the presence in the molecule of an amino acid ester group, to compositions containing them, to processes for their preparation and to their use in medicine as IKK inhibitors for the treatment of autoimmune and inflammatory diseases, including chronic obstructive pulmonary disease, asthma, rheumatoid arthritis, psoriasis, inflammatory bowel disease, Crohn's disease, ulcerative colitis, multiple sclerosis, diabetes, atopic dermatitis, graft versus host disease, systemic lupus erythematosus. The compounds are also of use in the treatment of proliferative disease states, such as cancers.

BACKGROUND OF THE INVENTION

The expression of many pro-inflammatory genes is regulated by the transcriptional activator nuclear factor-kB (NF-kB). These transcription factors have been suspected since their discovery to play a pivotal role in chronic and acute inflammatory diseases. It now seems that aberrant regulation of NF-kB could also underlie autoimmune diseases and different types of cancer.

Examples of genes dependent on the activation of NF-kB include: the cytokines tumor necrosis factor TNF-α, interleukin (IL)-6, IL-8 and IL-1β; the adhesion molecules E-selectin, intercellular adhesion molecule (ICAM)-1 and vascular cell adhesion molecule (VCAM)-1; and the enzymes nitric oxide synthase (NOS) and cyclooxygenase (COX)-2. NF-kB normally resides in the cytoplasm of unstimulated cells as an inactive complex with a member of the IkB inhibitory protein family. However, upon cellular activation, IkB is phosphorylated by the IkB kinase (IKK) and is subsequently degraded. Free NF-kB then translocates to the nucleus where it mediates pro-inflammatory gene expression.

There are three classical IkB's: IkBα, IkBβ and IkBε; all of which require the phosphorylation of two key serine residues before they can be degraded. Two major enzymes IKK-α and IKK-β appear to be responsible for IkB phosphorylation. Dominant-negative (DN) versions of either of these enzymes (where ATP binding is disabled by the mutation of a key kinase domain residue) were found to suppress the activation of NF-kB by TNF-α, IL-1β and LPS. Importantly IKK-β DN was found to be a far more potent inhibitor than IKK-α DN (Zandi, E *Cell*, 1997, 91, 243). Furthermore, the generation of IKK-α and IKK-β deficient mice established the requirement of IKK-β for activation of NF-kB by proinflammatory stimuli and reinforced the dominant role of IKK-β suggested by biochemical data. Indeed it was demonstrated that IKK-α was dispensable for NF-kB activation by these stimuli (Tanaka, M.; *Immunity* 1999, 10, 421). Thus, inhibition of IKK-β represents a potentially attractive target for modulation of immune function and hence the development of drugs for the treatment of auto-immune diseases.

BRIEF DESCRIPTION OF THE INVENTION

This invention makes available a class of thiophene carboxamides which are potent and selective inhibitors of IKK isoforms, particularly IKKβ. The compounds are thus of use in medicine, for example in the treatment of a variety of proliferative disease states, such as conditions related to the hyperactivity of IKK, as well as diseases modulated by the NF-kB cascade. In addition, the compounds of the invention are useful for the treatment of stroke, osteoporosis, rheumatoid arthritis and other inflammatory disorders. The compounds are characterised by the presence in the molecule of an amino acid motif or an amino acid ester motif which is hydrolysable by an intracellular carboxylesterase. Compounds of the invention having the lipophilic amino acid ester motif cross the cell membrane, and are hydrolysed to the acid by the intracellular carboxylesterases. The polar hydrolysis product accumulates in the cell since it does not readily cross the cell membrane. Hence the IKK inhibitory activity of the compound is prolonged and enhanced within the cell. The compounds of the invention are related to the IKK inhibitors encompassed by the disclosure in International Patent Application No. WO 2004063186 but differ therefrom in that the present compounds have the amino acid ester motif referred to above.

DETAILED DESCRIPTION OF THE INVENTION

According to the present invention there is provided compound of formula (IA) or (IB), or a salt, N-oxide, hydrate or solvate thereof:

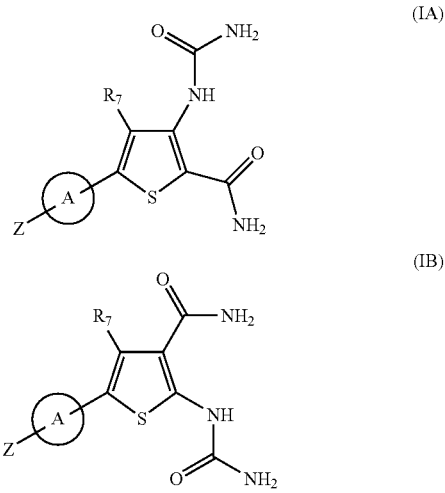

wherein $R_7$ is hydrogen or optionally substituted $(C_1$-$C_6)$alkyl;

ring A is an optionally substituted aryl or heteroaryl ring or ring system of 5-13 ring atoms;

Z is a radical of formula $R$-$L^1$-$Y^1$—$(CH_2)_z$—, wherein:

R is a radical of formula (X) or (Y)

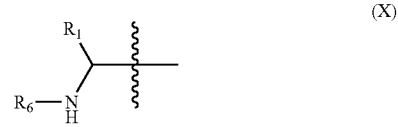

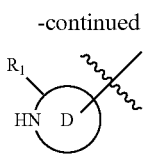

(Y)

R$_1$ is a carboxylic acid group (—COOH), or an ester group which is hydrolysable by one or more intracellular esterase enzymes to a carboxylic acid group;

R$_5$ is hydrogen; or optionally substituted C$_1$-C$_6$ alkyl, C$_3$-C$_7$ cycloalkyl, aryl or heteroaryl or —(C=O)R$_3$, —(C=O)OR$_3$, or —(C=O)NR$_3$ wherein R$_3$ is hydrogen or optionally substituted (C$_1$-C$_6$)alkyl, Y$^1$ is a bond, —(C=O)—, —S(O$_2$)—, —C(=O)O—, —OC(=O)—, —(C=O)NR$_3$—, —NR$_3$(C=O)—, —S(O$_2$)NR$_3$—, —NR$_3$S(O$_2$)—, or —NR$_3$(C=O)NR$_4$—, wherein R$_3$ and R$_4$ are independently hydrogen or optionally substituted (C$_1$-C$_6$)alkyl, L$^1$ is a divalent radical of formula -(Alk$^1$)$_m$(Q)$_n$(Alk$^2$)$_p$- wherein m, n and p are independently 0 or 1, Q is (i) an optionally substituted divalent mono- or bicyclic carbocyclic or heterocyclic radical having 5-13 ring members, or (ii), in the case where p is 0, a divalent radical of formula -Q$^1$-X$^2$— wherein X$^2$ is —O—, —S— or NR$^A$— wherein R$^A$ is hydrogen or optionally substituted C$_1$-C$_3$ alkyl, and Q$^1$ is an optionally substituted divalent mono- or bicyclic carbocyclic or heterocyclic radical having 5-13 ring members, Alk$^1$ and Alk$^2$ independently represent optionally substituted divalent C$_3$-C$_7$ cycloalkyl radicals, or optionally substituted straight or branched, C$_1$-C$_6$ alkylene, C$_2$-C$_6$ alkenylene, or C$_2$-C$_6$ alkynylene radicals which may optionally contain or terminate in an ether (—O—), thioether (—S—) or amino (—NR$^A$—) link wherein R$^A$ is hydrogen or optionally substituted C$_1$-C$_3$ alkyl; and z is 0 or 1.

In another broad aspect the invention provides the use of a compound of formula (IA) or (IB) as defined above, or an N-oxide, salt, hydrate or solvate thereof in the preparation of a composition for inhibiting the activity of IKK, especially IKKβ, as well as diseases modulated by the NF-kB cascade.

The compounds with which the invention is concerned may be used for the inhibition of IKK, especially IKKβ, activity in vitro or in vivo.

Pharmaceutical compositions comprising a compound of the invention together with one or more pharmaceutically acceptable carriers and excipients, also form part of the invention.

In one aspect of the invention, the compounds of the invention may be used in the preparation of a composition for the treatment of neoplastic/proliferative, autoimmune or inflammatory disease, particularly those mentioned above in which IKK, especially IKKβ, activity plays a role.

In another aspect, the invention provides a method for the treatment of the foregoing disease types, which comprises administering to a subject suffering such disease an effective amount of a compound of formula (IA) or (IB) as defined above.

Terminology

As used herein, the term "(C$_a$-C$_b$)alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "divalent (C$_a$-C$_b$)alkylene radical" wherein a and b are integers refers to a saturated hydrocarbon chain having from a to b carbon atoms and two unsatisfied valences.

As used herein the term "(C$_a$-C$_b$)alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "divalent (C$_a$-C$_b$)alkenylene radical" means a hydrocarbon chain having from a to b carbon atoms, at least one double bond, and two unsatisfied valences.

As used herein the term "(C$_a$-C$_b$)alkynyl" wherein a and b are integers refers to straight chain or branched chain hydrocarbon groups having from a to b carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent (C$_a$-C$_b$)alkynylene radical" wherein a and b are integers refers to a divalent hydrocarbon chain having from a to b carbon atoms, and at least one triple bond.

As used herein the term "carbocyclic" refers to a mono-, bi- or tricyclic radical having up to 16 ring atoms, all of which are carbon, and includes aryl and cycloalkyl.

As used herein the term "cycloalkyl" refers to a monocyclic saturated carbocyclic radical having from 3-8 carbon atoms and includes, for example, cyclopropyl, cyclobutyl, cyclopentyl, cyclohexyl, cycloheptyl and cyclooctyl.

As used herein the unqualified term "aryl" refers to a mono-, bi- or tri-cyclic carbocyclic aromatic radical, and includes radicals having two monocyclic carbocyclic aromatic rings which are directly linked by a covalent bond. Illustrative of such radicals are phenyl, biphenyl and napthyl.

As used herein the unqualified term "heteroaryl" refers to a mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzothienyl, furyl, benzofuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in its non-aromatic meaning relates to a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzofuranyl, pyranyl, isoxazolyl, benzimidazolyl, methylenedioxyphenyl, ethylenedioxyphenyl, maleimido and succinimido groups.

A "divalent phenylene, pyridinylene, pyrimidinylene, or pyrazinylene radical" is a benzene, pyridine, pyrimidine or pyrazine ring, with two unsatisfied valencies, and includes 1,3-phenylene, 1,4-phenylene, and the following:

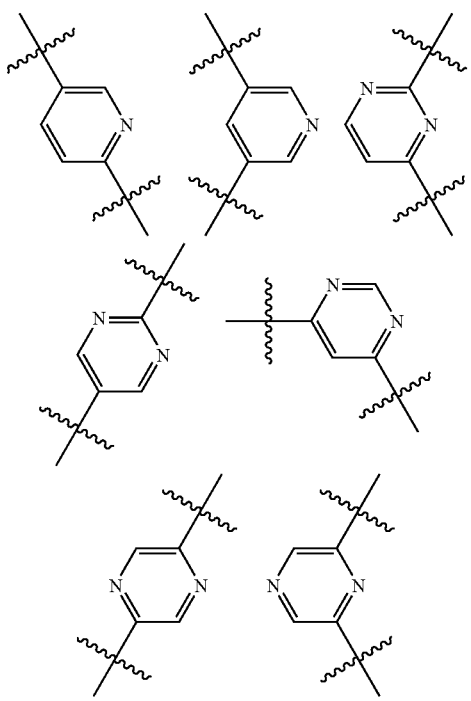

Unless otherwise specified in the context in which it occurs, the term "substituted" as applied to any moiety herein means substituted with up to four compatible substituents, each of which independently may be, for example, $(C_1-C_6)$ alkyl, $(C_1-C_6)$alkoxy, hydroxy, hydroxy$(C_1-C_6)$alkyl, mercapto, mercapto$(C_1-C_6)$alkyl, $(C_1-C_6)$alkylthio, phenyl, halo (including fluoro, bromo and chloro), trifluoromethyl, trifluoromethoxy, nitro, nitrile (—CN), oxo, —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OH, —NR$^B$SO$_2$OR$^A$, —NH-CONH$_2$, —NR$^A$CONH$_2$, —NHCONHR$^B$, —NR$^A$CONHR$^B$, —NHCONR$^A$R$^B$, or —NR$^A$CONR$^A$R$^B$ wherein R$^A$ and R$^B$ are independently a $(C_1-C_6)$alkyl, $(C_3-C_6)$ cycloalkyl, phenyl or monocyclic heteroaryl having 5 or 6 ring atoms, or R$^A$ and R$^B$ when attached to the same nitrogen atom form a cyclic amino group (for example morpholino, piperidinyl, piperazinyl, or tetrahydropyrrolyl). An "optional substituent" may be one of the foregoing substituent groups.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Those compounds (IA) and (IB) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids and the like.

It is expected that compounds of the invention may be recovered in hydrate or solvate form. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Compounds of the invention which contain one or more actual or potential chiral centres, because of the presence of asymmetric carbon atoms, can exist as a number of diastereoisomers with R or S stereochemistry at each chiral centre. The invention includes all such diastereoisomers and mixtures thereof.

The term "ester" or "ester group" or "esterified carboxyl group" in connection with substituent R$_1$ above means a group R$_x$O(C=O)— in which R$_x$ is the group characterising the ester, notionally derived from the alcohol R$_x$OH.

In the compounds of the invention, the variable substituents and groups will now be discussed in more detail:

The Substituent R$_7$

R$_7$ is hydrogen or optionally substituted $(C_1-C_6)$alkyl, such as methyl, ethyl or n- or iso-propyl. Currently preferred is when R$_7$ is hydrogen.

The Ring A

Ring A is an optionally substituted divalent aryl or heteroaryl ring of 5-13 atoms, such as a monocyclic 5- or 6-membered ring or a bicyclic 5,6-, 6,6-, or 5,5-ring system. Examples include divalent phenylene, pyridinylene, pyrimidinylene, and pyrazinylene radicals. Currently preferred is 1,4-phenylene or 1,3-phenylene. Optional substituents in ring A may be selected from, for example fluoro, chloro, methyl, and trifluoromethyl.

The Group Z

The Group R$_1$ in Z

R$_1$ is a carboxylic acid group or an ester group which is hydrolysable by one or more intracellular carboxylesterase enzymes to a carboxylic acid group. Intracellular carboxylesterase enzymes capable of hydrolysing the ester group of a compound of the invention to the corresponding acid include the three known human enzyme isotypes hCE-1, hCE-2 and hCE-3. Although these are considered to be the main enzymes, other enzymes such as biphenylhydrolase (BPH) may also have a role in hydrolysing the ester. In general, if the carboxylesterase hydrolyses the free amino acid ester to the parent acid it will also hydrolyse the ester motif when covalently conjugated to the IKK inhibitor. Hence, the broken cell assay described herein provides a straightforward, quick and simple first screen for esters which have the required hydrolysis profile. Ester motifs selected in that way may then be re-assayed in the same carboxylesterase assay when conjugated to the modulator via the chosen conjugation chemistry, to confirm that it is still a carboxylesterase substrate in that background.

Subject to the requirement that they be hydrolysable by intracellular carboxylesterase enzymes, examples of particular ester groups R$_1$ include those of formula —(C=O)OR$_{14}$ wherein R$_{14}$ is R$_8$R$_9$R$_{10}$C— wherein (i) R$_8$ is hydrogen or optionally substituted $(C_1-C_3)$alkyl-$(Z^1)_a$—[$(C_1-C_3)$alkyl]$_b$- or $(C_2-C_3)$alkenyl-$(Z^1)_a$—[$(C_1-C_3)$alkyl]$_b$- wherein a and b are independently 0 or 1 and Z$^1$ is —O—, —S—, or —NR$_{11}$— wherein R$_{11}$ is hydrogen or $(C_1-C_3)$alkyl; and R$_9$ and R$_{10}$ are independently hydrogen or $(C_1-C_3)$alkyl-;

(ii) $R_8$ is hydrogen or optionally substituted $R_{12}R_{13}N$—($C_1$-$C_3$)alkyl- wherein $R_{12}$ is hydrogen or ($C_1$-$C_3$)alkyl and $R_{13}$ is hydrogen or ($C_1$-$C_3$)alkyl; or $R_{12}$ and $R_{13}$ together with the nitrogen to which they are attached form an optionally substituted monocyclic heterocyclic ring of 5- or 6-ring atoms or bicyclic heterocyclic ring system of 8 to 10 ring atoms, and $R_9$ and $R_{10}$ are independently hydrogen or ($C_1$-$C_3$)alkyl-; or (iii) $R_8$ and $R_9$ taken together with the carbon to which they are attached form an optionally substituted monocyclic carbocyclic ring of from 3 to 7 ring atoms or bicyclic carbocyclic ring system of 8 to 10 ring atoms, and $R_{10}$ is hydrogen.

$R_1$ may be, for example, a methyl, ethyl, n- or iso-propyl, n-, sec- or tert-butyl, cyclohexyl, allyl, phenyl, benzyl, 2-, 3- or 4-pyridylmethyl, N-methylpiperidin-4-yl, tetrahydrofuran-3-yl, methoxyethyl, indanyl, norbornyl, dimethylaminoethyl, or morpholinoethyl ester group. Cyclopentyl or tert-butyl esters are currently preferred.

The Ring D in Z

When R is a group of formula (Y), examples of R include:

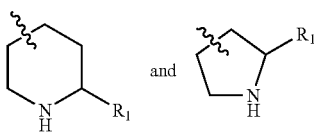

wherein $R_1$ is as defined and discussed above.

The Group $R_6$ in Z $R_6$ may be optionally substituted $C_1$-$C_6$ alkyl, $C_3$-$C_7$ cycloalkyl, aryl or heteroaryl, for example methyl, ethyl, n- or isopropyl, cyclopropyl, cyclopentyl, cyclohexyl, phenyl, or pyridyl. In cases where macrophage specificity is not required, $R_6$ may be hydrogen or —C(=O)$R^D$, wherein $R^D$ is optionally substituted ($C_1$-$C_6$)alkyl such as methyl, ethyl, n- or isopropyl, or n-, iso- or sec-butyl, ($C_3$-$C_7$)cycloalkyl such as cyclopropyl, cyclopentyl, cyclohexyl, phenyl, pyridyl, thienyl, phenyl($C_1$-$C_6$ alkyl)-, thienyl($C_1$-$C_6$ alkyl)- or pyridyl($C_1$-$C_6$ alkyl)- such as benzyl, 4-methoxyphenylmethylcarbonyl, thienylmethyl or pyridylmethyl.

$R_6$ may also be, for example —C(=O)O$R^D$, or —C(=O)NH$R^D$ wherein $R^D$ is hydrogen or optionally substituted ($C_1$-$C_6$)alkyl such as methyl, ethyl, or n- or isopropyl.

For compounds of the invention which are to be administered systemically, esters with a slow rate of esterase cleavage are preferred, since they are less susceptible to pre-systemic metabolism. Their ability to reach their target tissue intact is therefore increased, and the ester can be converted inside the cells of the target tissue into the acid product. However, for local administration, where the ester is either directly applied to the target tissue or directed there by, for example, inhalation, it will often be desirable that the ester has a rapid rate of esterase cleavage, to minimise systemic exposure and consequent unwanted side effects. If a carbon atom to which the group R is attached is unsubstituted, i.e. R is attached to a methylene (—CH$_2$)— radical, then the esters tend to be cleaved more rapidly than if that carbon is substituted, or is part of a ring system such as a phenyl or cyclohexyl ring.

The Radical -L$^1$-Y$^1$—[CH$_2$]$_z$— in Z

This radical (or bond) arises from the particular chemistry strategy chosen to link the amino acid ester motif R in substituent Z to the rest of the molecule. Clearly the chemistry strategy for that coupling may vary widely, and thus many combinations of the variables Y$^1$, L$^1$, and z are possible. However, when the inhibitor is bound to the enzyme at its active site, the amino acid ester motif generally extends in a direction away from the enzyme, and thus minimises or avoids interference with the binding mode of the inhibitor. Hence the precise combination of variable making up the linking chemistry between the amino acid ester motif and the rest of the molecule will often be irrelevant to the primary binding mode of the compound as a whole.

With the foregoing general observations in mind, taking the variables making up the radical -L$^1$-Y$^1$—[CH$_2$]$_z$— in turn:

z may be 0 or 1, so that a methylene radical linked to the rest of the molecule is optional;

Y$^1$ may be, for example, —NR$_3$—, —S—, —O—, —C(=O)NR$_3$—, —NR$_3$C(=O)—, or —C(=O)O—, wherein R$_3$ is hydrogen or optionally substituted C$_1$-C$_6$ alkyl such as —CH$_2$CH$_2$OH;

In the radical L$^1$, examples of Alk$^1$ and Alk$^2$ radicals, when present, include —CH$_2$—, —CH$_2$CH$_2$—, —CH$_2$CH$_2$CH$_2$—, —CH$_2$CH$_2$CH$_2$CH$_2$—, —CH=CH—, —CH=CHCH$_2$—, —CH$_2$CH=CH—, CH$_2$CH=CHCH$_2$—, —C≡C—, —C≡CCH$_2$—, CH$_2$C≡C—, and CH$_2$C≡CCH$_2$—. Additional examples of Alk$^1$ and Alk$^2$ include —CH$_2$W—, —CH$_2$CH$_2$W—, —CH$_2$CH$_2$WCH$_2$—, —CH$_2$CH$_2$WCH(CH$_3$)—, —CH$_2$WCH$_2$CH$_2$—, —CH$_2$WCH$_2$CH$_2$WCH$_2$—, and —WCH$_2$CH$_2$— where W is —O—, —S—, —NH—, —N(CH$_3$)—, or —CH$_2$CH$_2$N(CH$_2$CH$_2$OH)CH$_2$—. Further examples of Alk$^1$ and Alk$^2$ include divalent cyclopropyl, cyclopentyl and cyclohexyl radicals.

Alk$^1$ and Alk$^2$ when present may also be branched chain alkyl such as —CH(CH$_3$)—, —C(CH$_3$)$_2$—, or in either orientation —CH$_2$CH(CH$_3$)—, —CH$_2$C(CH$_3$)$_2$—.

In L$^1$, when n is 0, the radical is a hydrocarbon chain (optionally substituted and perhaps having an ether, thioether or amino linkage). Presently it is preferred that there be no optional substituents in L$^1$. When both m and p are 0, L$^1$ is a divalent mono- or bicyclic carbocyclic or heterocyclic radical with 5-13 ring atoms (optionally substituted). When n is 1 and at least one of m and p is 1, L$^1$ is a divalent radical including a hydrocarbon chain or chains and a mono- or bicyclic carbocyclic or heterocyclic radical with 5-13 ring atoms (optionally substituted). When present, Q may be, for example, a divalent phenyl, naphthyl, cyclopropyl, cyclopentyl, or cyclohexyl radical, or a mono-, or bi-cyclic heterocyclic radical having 5 to 13 ring members, such as piperidinyl, piperazinyl, indolyl, pyridyl, thienyl, or pyrrolyl radical, but 1,4-phenylene is presently preferred.

Specifically, in some embodiments of the invention, L$^1$, m and p may be 0 with n being 1. In other embodiments, n and p may be 0 with m being 1. In further embodiments, m, n and p may be all 0. In still further embodiments m may be 0, n may be 1 with Q being a monocyclic heterocyclic radical, and p may be 0 or 1. Alk$^1$ and Alk$^2$, when present, may be selected from —CH$_2$—, —CH$_2$CH$_2$—, and —CH$_2$CH$_2$CH$_2$— and Q may be 1,4-phenylene.

Specific examples of the radical -L$^1$-Y$^1$—[CH$_2$]$_z$— include

-L$_1$-Y$^1$—(CH$_2$)$_z$— in Z is —(CH$_2$)$_a$(O)$_d$(CH$_2$)$_a$ wherein a is 1, 2 or 3, b is 0, 1 or 2, and d is 0 or 1, —CH=CH—, or —CH$_2$CH=CH—. —CH=CHCH$_2$—, —C≡C—, —CH$_2$C≡C—, —C≡CCH$_2$—, —(CH$_2$)$_3$NH—, —CH$_2$C(=O)NH—, —CH$_2$CH$_2$C(=O)NH—, —CH$_2$C(O)O—, —CH$_2$S—, —CH$_2$CH$_2$C(O)O—, —(CH$_2$)$_4$NH—, —CH$_2$CH$_2$S—,

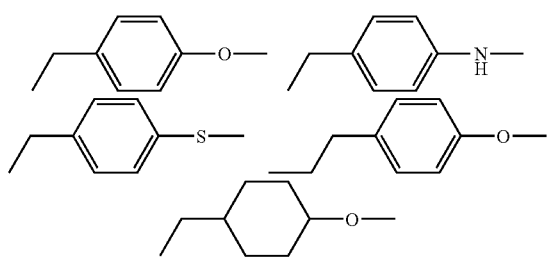

Specific compounds of the invention include those of the examples herein, their salts, N-oxides, hydrates and solvates.

As mentioned above, the compounds with which the invention is concerned are inhibitors of IKK, especially IKKβ kinase activity, and are therefore of use in the treatment of diseases modulated by IKK activity and the NF-kB cascade. Such diseases include neoplastic/proliferative, immune and inflammatory disease. In particular, uses of the compounds include treatment of cancers such as hepatocellular cancer or melanoma, but including bowel cancer, ovarian cancer, head and neck and cervical squamous cancers, gastric or lung cancers, anaplastic oligodendrogliomas, glioblastoma multiforme or medulloblastomas; and treatment of rheumatoid arthritis, psoriasis, inflammatory bowel disease, Crohn's disease, ulcerative colitis, chronic obstructive pulmonary disease, asthma, multiple sclerosis, diabetes, atopic dermatitis, graft versus host disease, or systemic lupus erythematosus.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The compounds of the invention may be administered in inhaled form. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0505321).

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agent can be dissolved in the vehicle.

The compounds of the invention may be used in conjunction with a number of known pharmaceutically active substances. For example, the compounds of the invention may be used with cytotoxics, HDAC inhibitors, kinase inhibitors, aminopeptidase inhibitors, protease inhibitors, bcl-2 antagonists, inhibitors of mTor and monoclonal antibodies (for example those directed at growth factor receptors). Preferred cytotoxics include, for example, taxanes, platins, anti-metabolites such as 5-fluoracil, topoisomerase inhibitors and the like. The medicaments of the invention comprising amino acid derivatives of formula (IA) or (IB), tautomers thereof or pharmaceutically acceptable salts, N-oxides, hydrates or solvates thereof therefore typically further comprise a cytotoxic, an HDAC inhibitor, a kinase inhibitor, an aminopeptidase inhibitor and/or a monoclonal antibody.

Further, the present invention provides a pharmaceutical composition comprising:
(a) an amino acid derivative of formula (IA) or (IB), or a pharmaceutically acceptable salt, N-oxide, hydrate or solvate thereof;
(b) a cytotoxic agent, an HDAC inhibitor, a kinase inhibitor, an aminopeptidase inhibitor, a protease inhibitor, a bcl-2 antagonist, an inhibitor of mTor and/or a monoclonal antibody; and
(c) a pharmaceutically acceptable carrier or diluent.

Also provided is a product comprising:
(a) an amino acid derivative of formula (IA) or (IB), or a pharmaceutically acceptable salt, N-oxide, hydrate or solvate thereof; and (b) a cytotoxic agent, an HDAC inhibitor, a kinase inhibitor, an aminopeptidase inhibitor, a protease inhibitor, a bcl-2 antagonist, an inhibitor of mTor and/or a monoclonal antibody, for the separate, simultaneous or sequential use in the treatment of the human or animal body.

Synthesis

There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to those skilled in the art. Typical literature sources are "Advanced organic chemistry", $4^{th}$ Edition (Wiley), J March, "Comprehensive Organic Transformation", $2^{nd}$ Edition (Wiley), R. C. Larock, "Handbook of Heterocyclic Chemistry", $2^{nd}$ Edition (Pergamon), A. R. Katritzky), review articles such as found in "Synthesis", "Acc. Chem. Res.", "Chem. Rev", or primary literature sources identified by standard literature searches online or from secondary sources such as "Chemical Abstract" or "Beilstein".

The compounds of the invention may be prepared by a number of processes generally described below and more specifically in the Examples hereinafter. In the reactions described below, it may be necessary to protect reactive functional groups, for example hydroxyl, amino and carboxy groups, where these are desired in the final product, to avoid their unwanted participation in the reactions [see for example Greene, T. W., "Protecting Groups in Organic Synthesis", John Wiley and Sons, 1999]. Conventional protecting groups may be used in conjunction with standard practice. In some instances deprotection may be the final step in the synthesis of a compound of general formula (IA) or (IB), and the processes according to the invention described herein after are understood to extend to such removal of protecting groups.

As mentioned above, the compounds with which the invention is concerned are inhibitors of the IkB family, namely IKK-α and IKK-β, and are therefore of use in the treatment of cell proliferative disease, such as cancer, and in treatment of inflammation, in humans and other mammals.

Abbreviations

MeOH=methanol

EtOH=ethanol

IPA=isopropyl alcohol

EtOAc=ethyl acetate

DCM=dichloromethane

DMF=dimethylformamide

DME=dimethyl ether

DMSO=dimethyl sulfoxide

DMAP=dimethylamino pyridine

TFA=trifluoroacetic acid

THF=tetrahydrofuran

FMOC=9-fluorenylmethoxycarbonyl $Na_2CO_3$=sodium carbonate

HCl=hydrochloric acid

DIPEA=diisopropylethylamine

MP-$CNBH_3$=macroporous triethylammonium methylpolystyrene cyanoborohydride

BEMP=2-tbutylimino-2-diethylamino-1,3-dimethyl-perhydro-1,3,2-diazaphosphorine

NaH=sodium hydride

NaOH=sodium hydroxide $NaHCO_3$=sodium hydrogen carbonate

HCl=hydrochloric acid

Pd/C=palladium on carbon $PdCl_2$(dppf)=[1,1'-Bis(diphenylphosphino)ferrocene]dichloropalladium(II).

EDC=1-ethyl-3-(3-dimethylaminopropyl)carbodiimide

KOAc=potassium acetate

TBAI=tetrabutyl ammonium iodide ml=milliliter(s)

g=gram(s)

mg=milligram(s)

mol=mole(s)

mmol=millimole(s)

Sat=saturated

LCMS=high performance liquid chromatography/mass spectrometry

NMR=nuclear magnetic resonance

Commercially available reagents and solvents (HPLC grade) were used without further purification. Solvents were removed using a Buchi rotary evaporator. Microwave irradiation was carried out using a CEM Discovery model set at 300 W. Purification of compounds by flash chromatography column was performed using silica gel, particle size 40-63μ μm (230-400 mesh) obtained from Fluorochem. Purification of compounds by preparative HPLC was performed on a Agilent prep system using reverse phase Agilent prep-C18 columns (5 μm, 50×21.2 mm), gradient 0-100% B (A=water/0.1% ammonia or 0.1% formic acid and B=acetonitrile/0.1% ammonia or 0.1% formic acid) over 10 min, flow=28 ml/min, UV detection at 254 nm.

$^1$H NMR spectra were recorded on a Bruker 400 or 300 MHz AV spectrometer in deuterated solvents. Chemical shifts (δ) are in parts per million. Thin-layer chromatography (TLC) analysis was performed with Kieselgel 60 $F_{254}$ (Merck) plates and visualized using UV light.

Analytical HPLC/MS were obtained as follows: Agilent Prep-C18 Scalar column, 5 μm (4.6×50 mm, flow rate 2.5 ml/min) eluting with a $H_2O$-MeCN gradient containing 0.1% v/v formic acid over 7 minutes with UV detection at 254 nm. Gradient information: 0.0-0.5 min: 95% $H_2O$-5% MeCN; 0.5-5.0 min; Ramp from 95% $H_2O$-5% MeCN to 5% $H_2O$-95% MeCN; 5.0-5.5 min: Hold at 5% $H_2O$-95% MeCN; 5.5-5.6 min: Hold at 5% $H_2O$-95% MeCN, flow rate increased to 3.5 ml/min; 5.6-6.6 min: Hold at 5% $H_2O$-95% MeCN, flow rate 3.5 ml/min; 6.6-6.75 min: Return to 95% $H_2O$-5% MeCN, flow rate 3.5 ml/min; 6.75-6.9 min: Hold at 95% $H_2O$-5% MeCN, flow rate 3.5 ml/min; 6.9-7.0 min: Hold at 95% $H_2O$-5% MeCN, flow rate reduced to 2.5 ml/min. Mass spectra were obtained using an Agilent multimode source in either the positive (APCI+ESI$^+$) or negative (APCI+ESI$^-$) mode.

Examples of such methods that may be employed in the synthesis of compounds of general formula (IA) and (IB) are set out, but not limited to the reactions shown in Schemes 1-10 below.

Scheme 1 illustrates the general synthetic route for the preparation of the examples described below, using traditional Suzuki chemistry to couple the relevant boronate ester intermediates (2a-5c and 7a-12) with the central thiophene core (Intermediates 1 and 13).

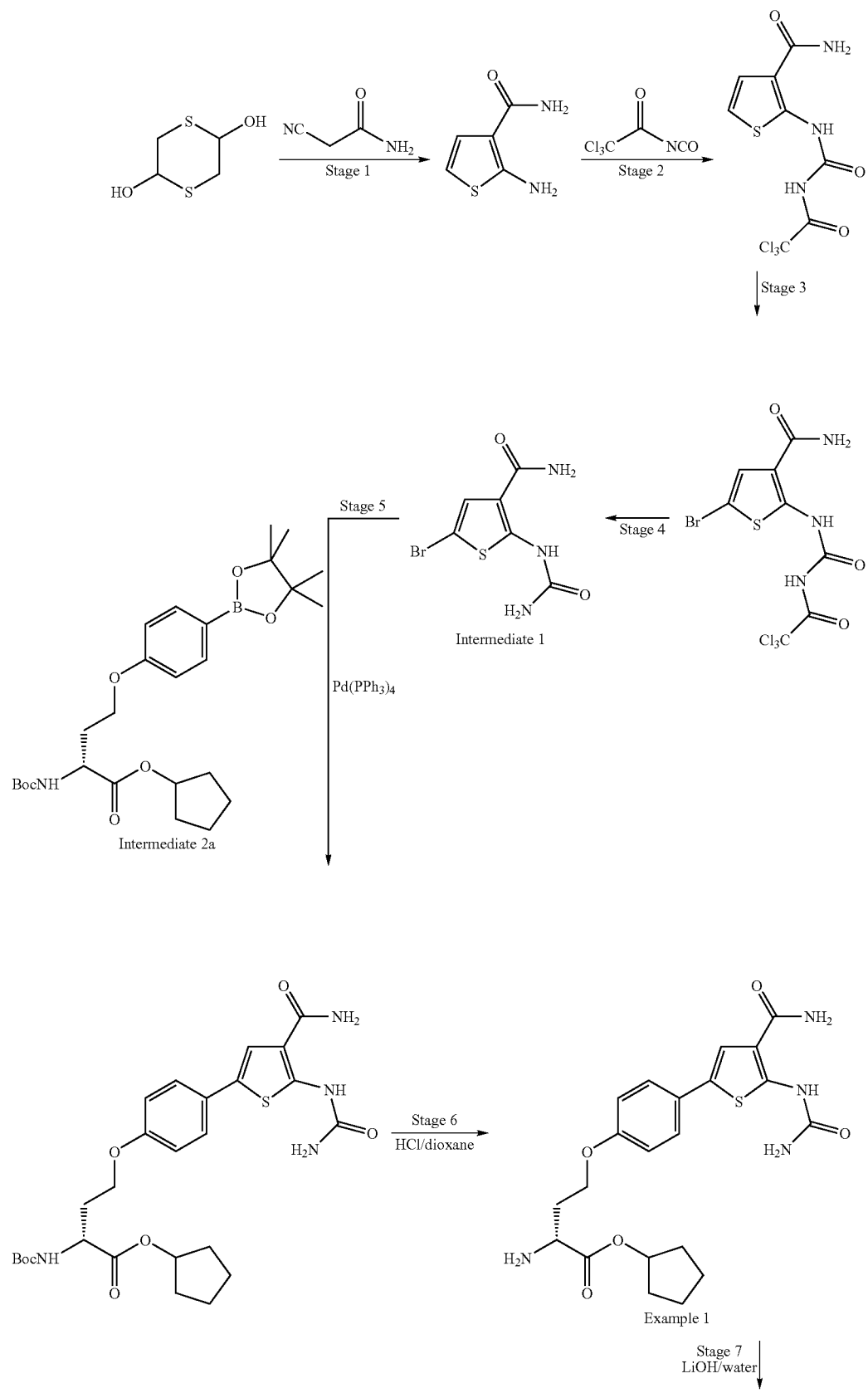

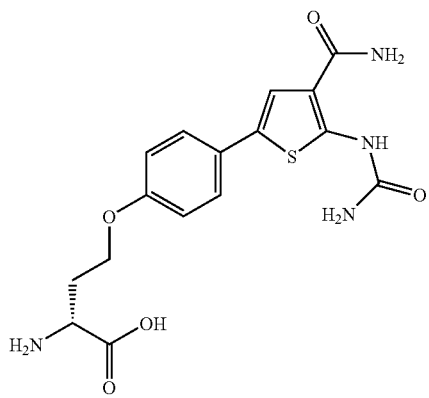
Example 25
Scheme 2 illustrates the synthesis to Intermediate 2a.
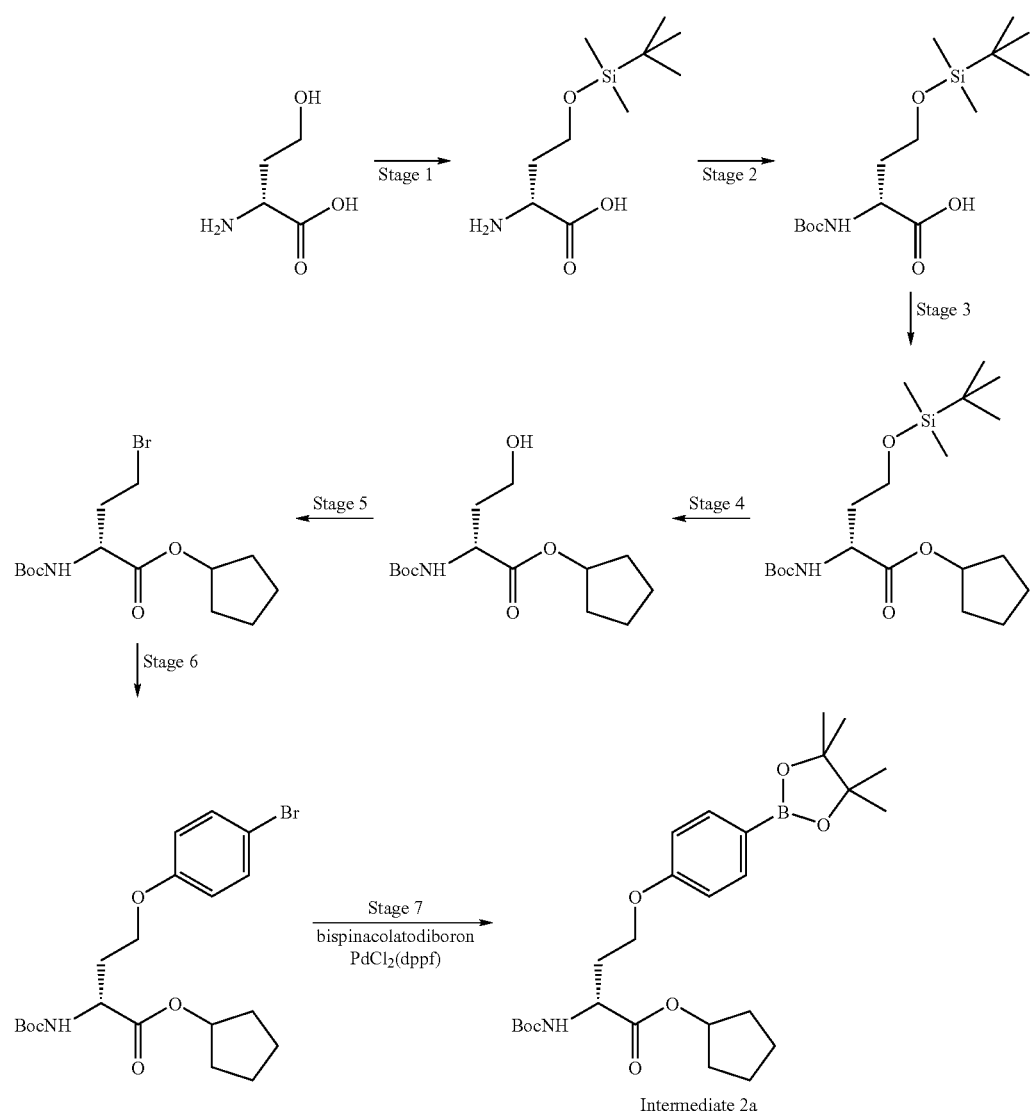
Intermediate 2a Scheme 3 illustrates the synthesis to Intermediate 3a.
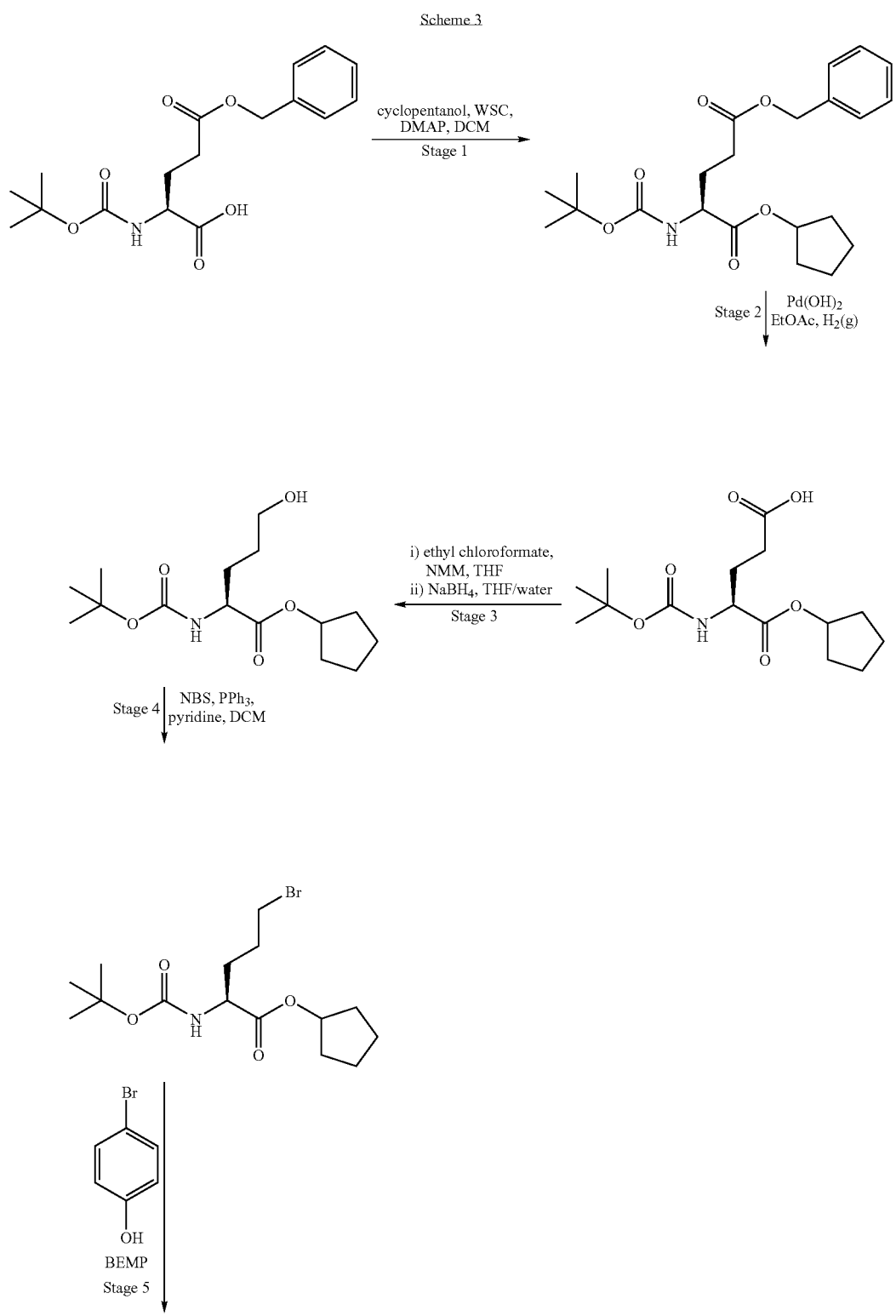

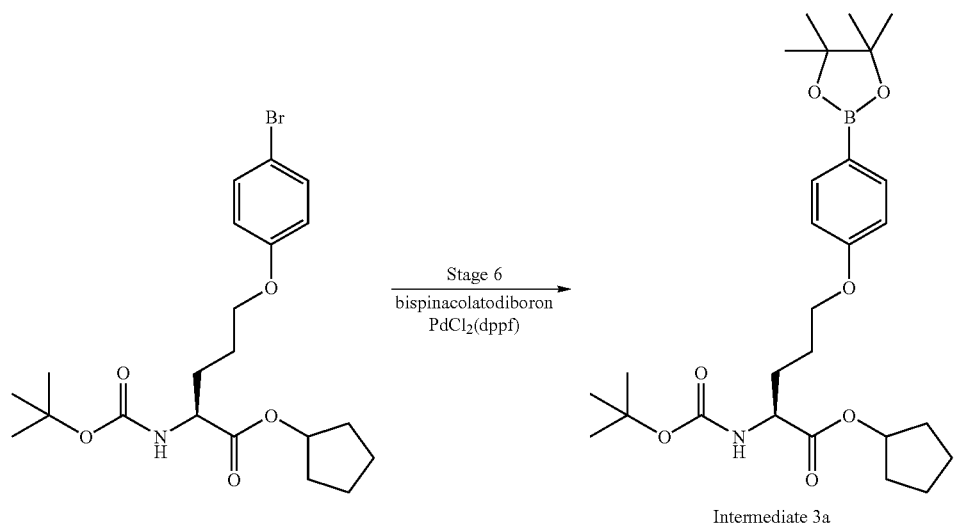
Scheme 4 illustrates the synthesis to Intermediate 5a.
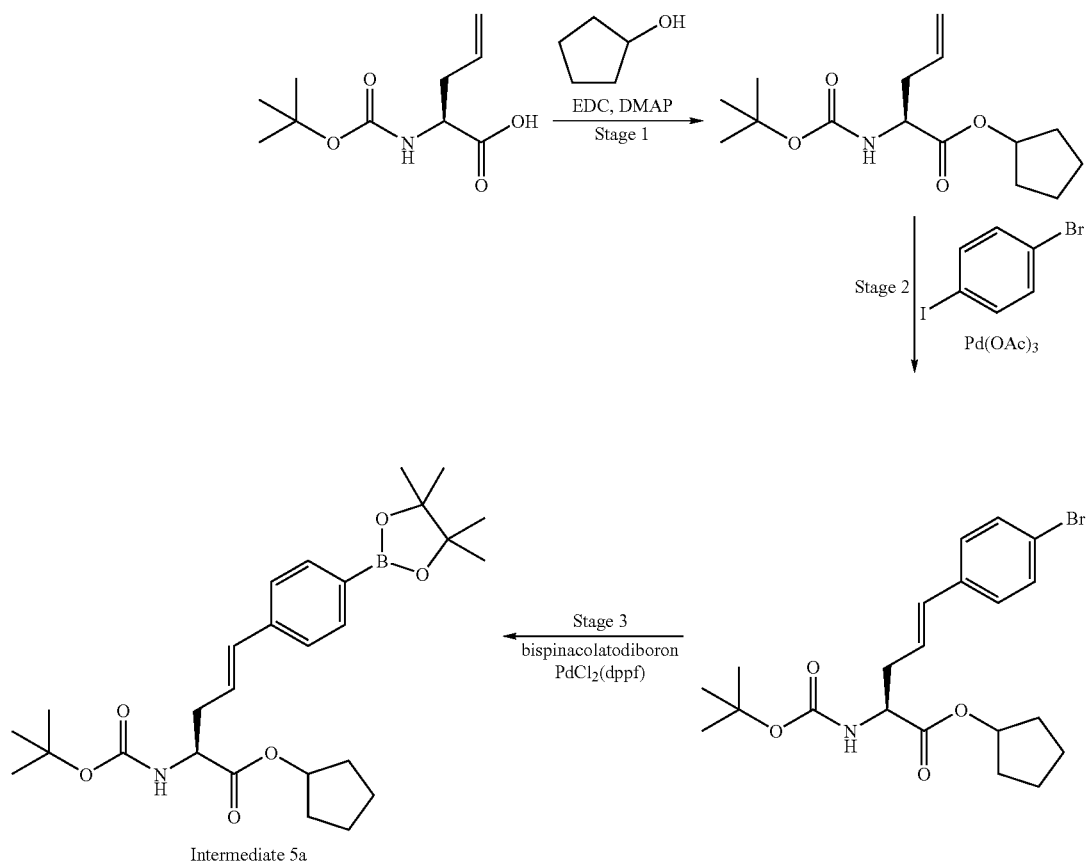

Scheme 5 illustrates the synthesis to Intermediate 6a.
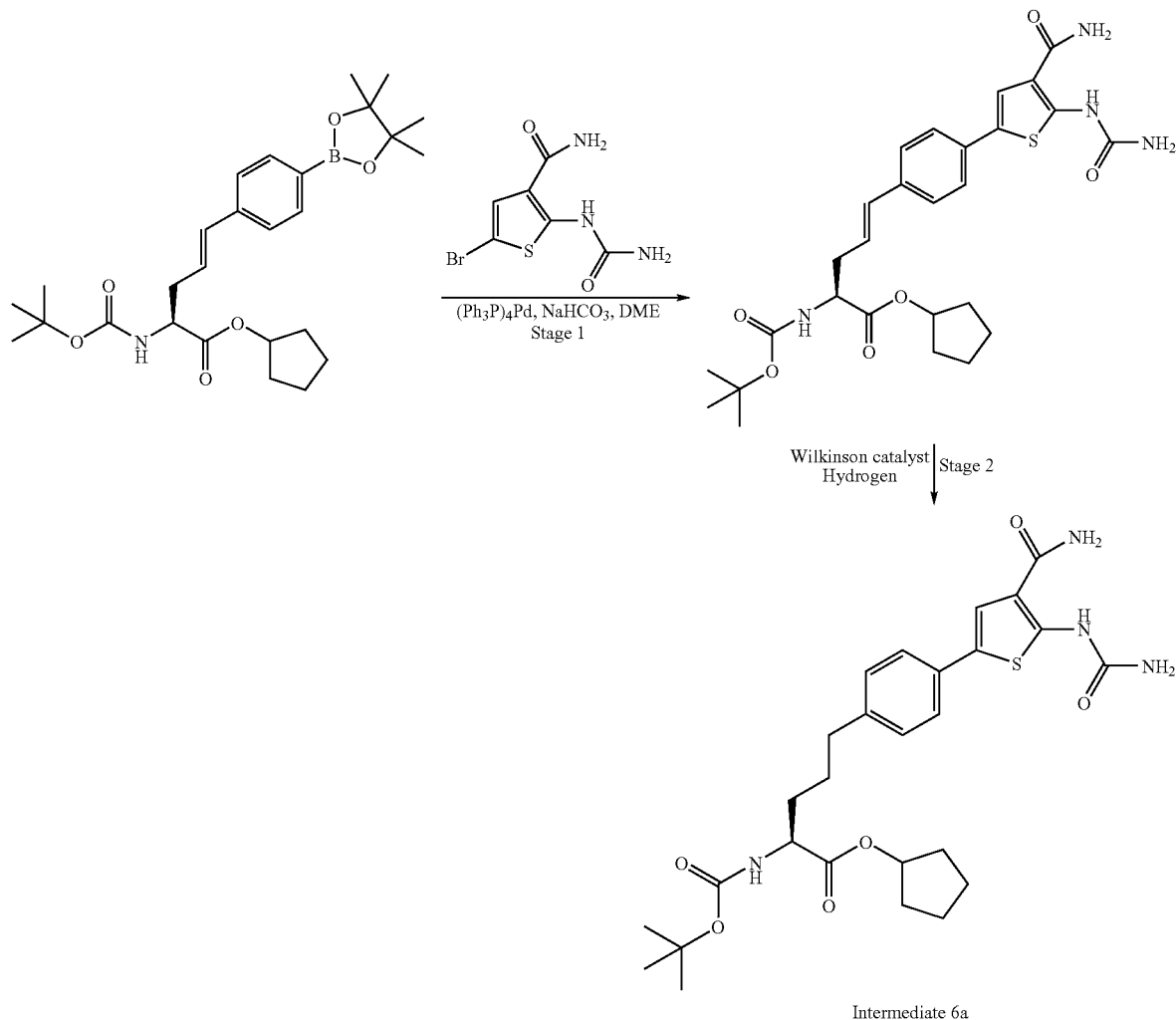
Intermediate 6a
Scheme 6 illustrates the synthesis to Intermediates 8 and 11.
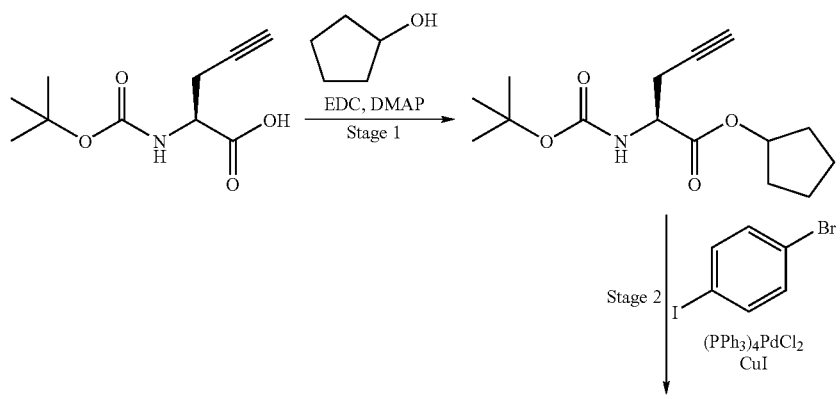

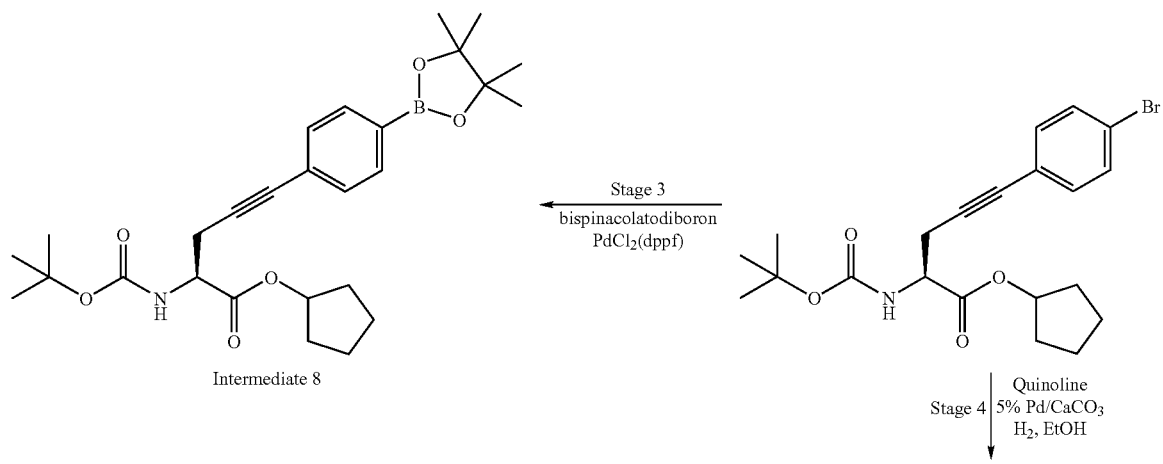
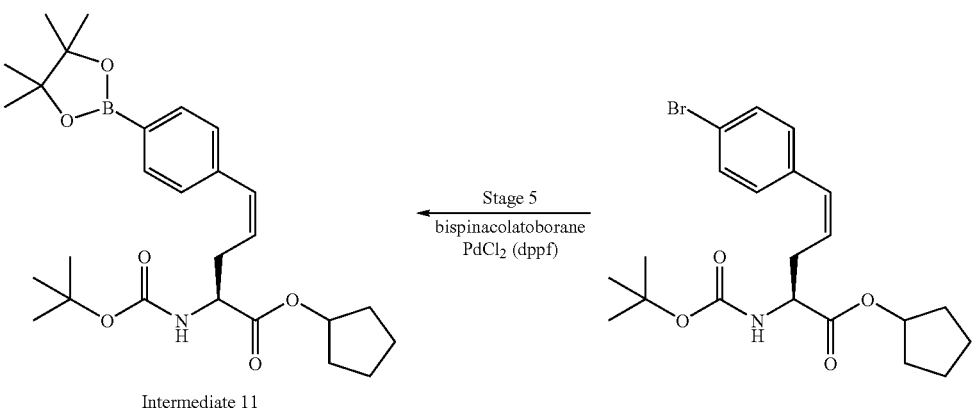
Scheme 7 illustrates the synthesis to Intermediate 9.
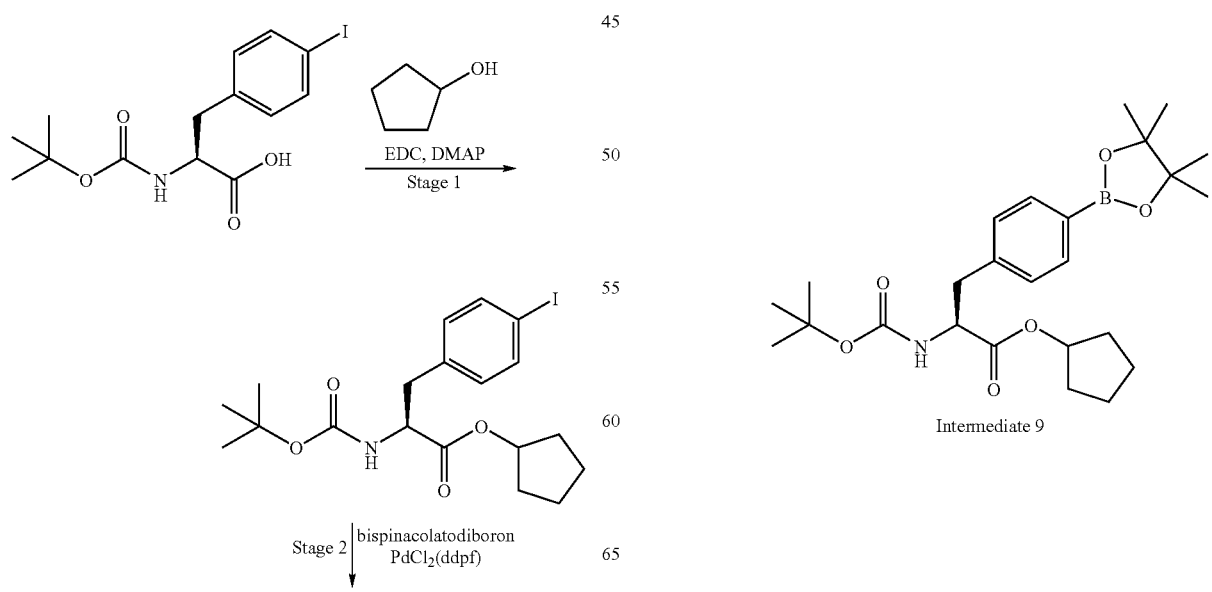

Scheme 8 illustrates the synthesis to Intermediate 10.
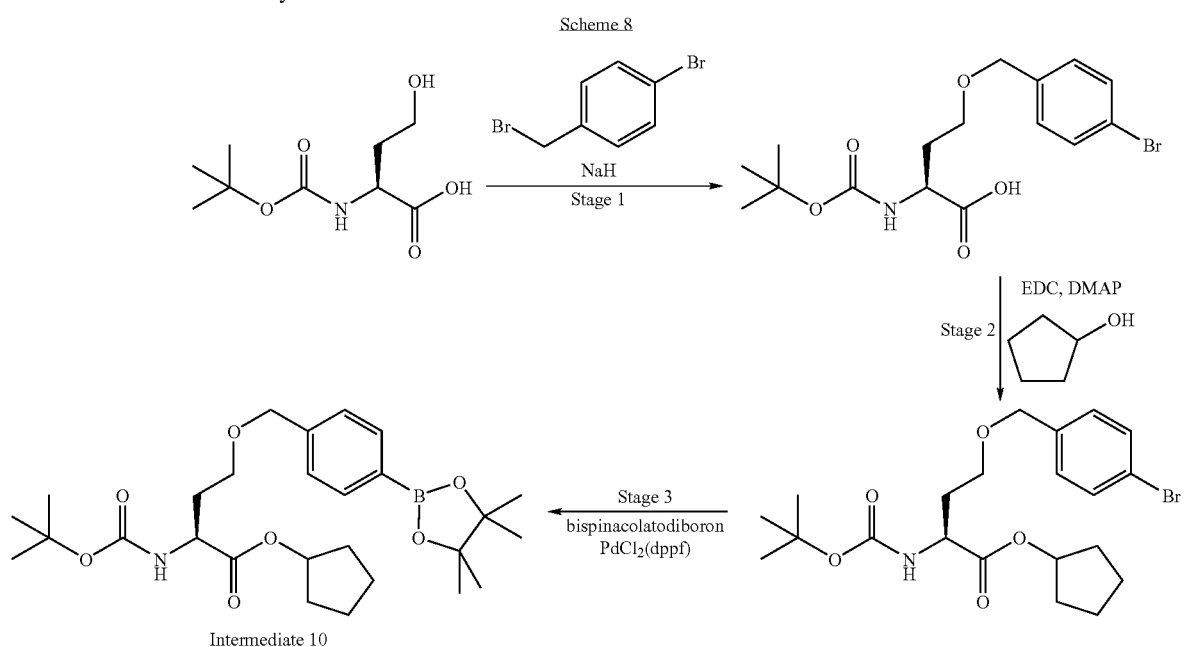
Scheme 9 illustrates the synthesis to Example 19.
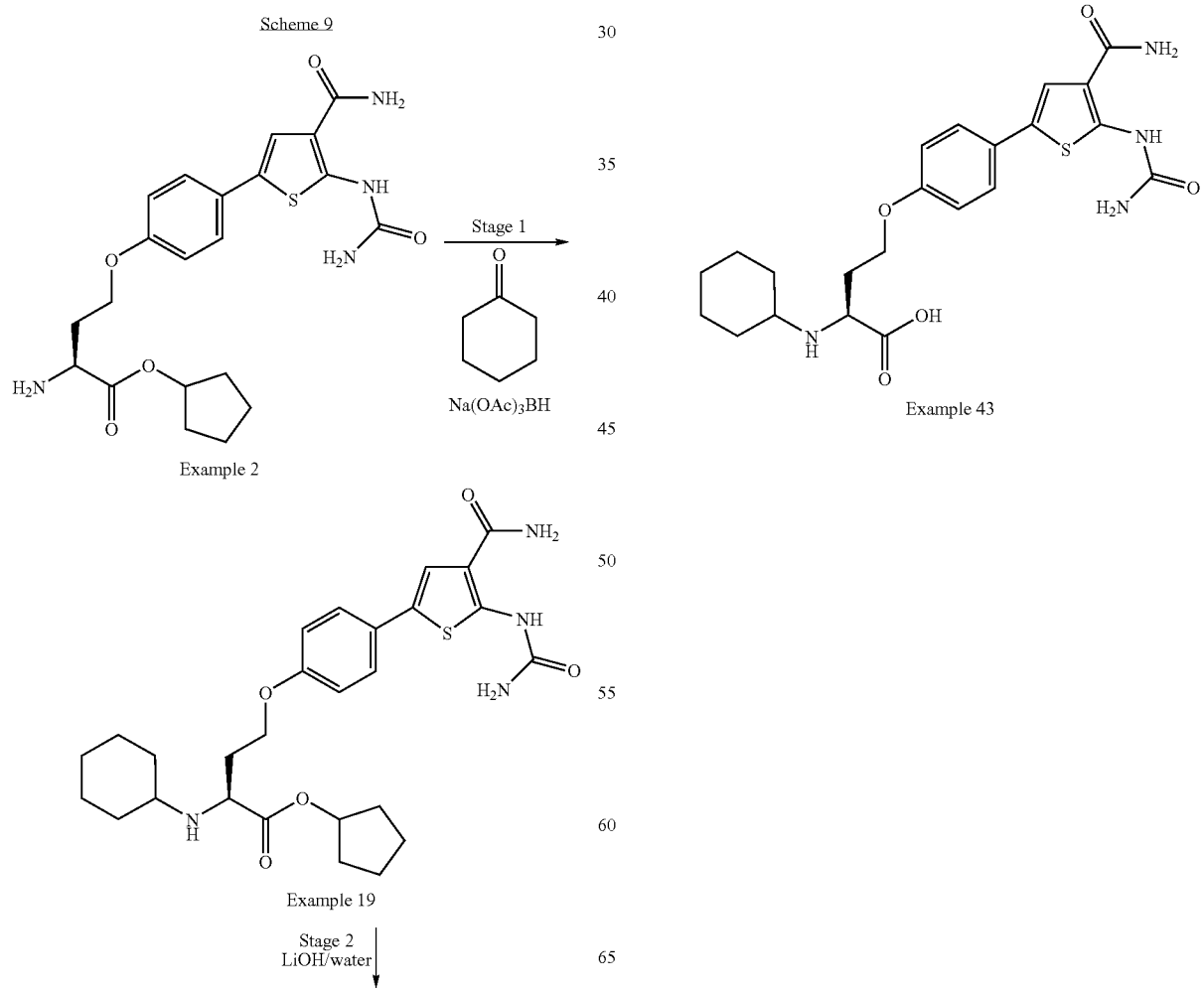

Scheme 10 illustrates the synthesis to Intermediate 12.
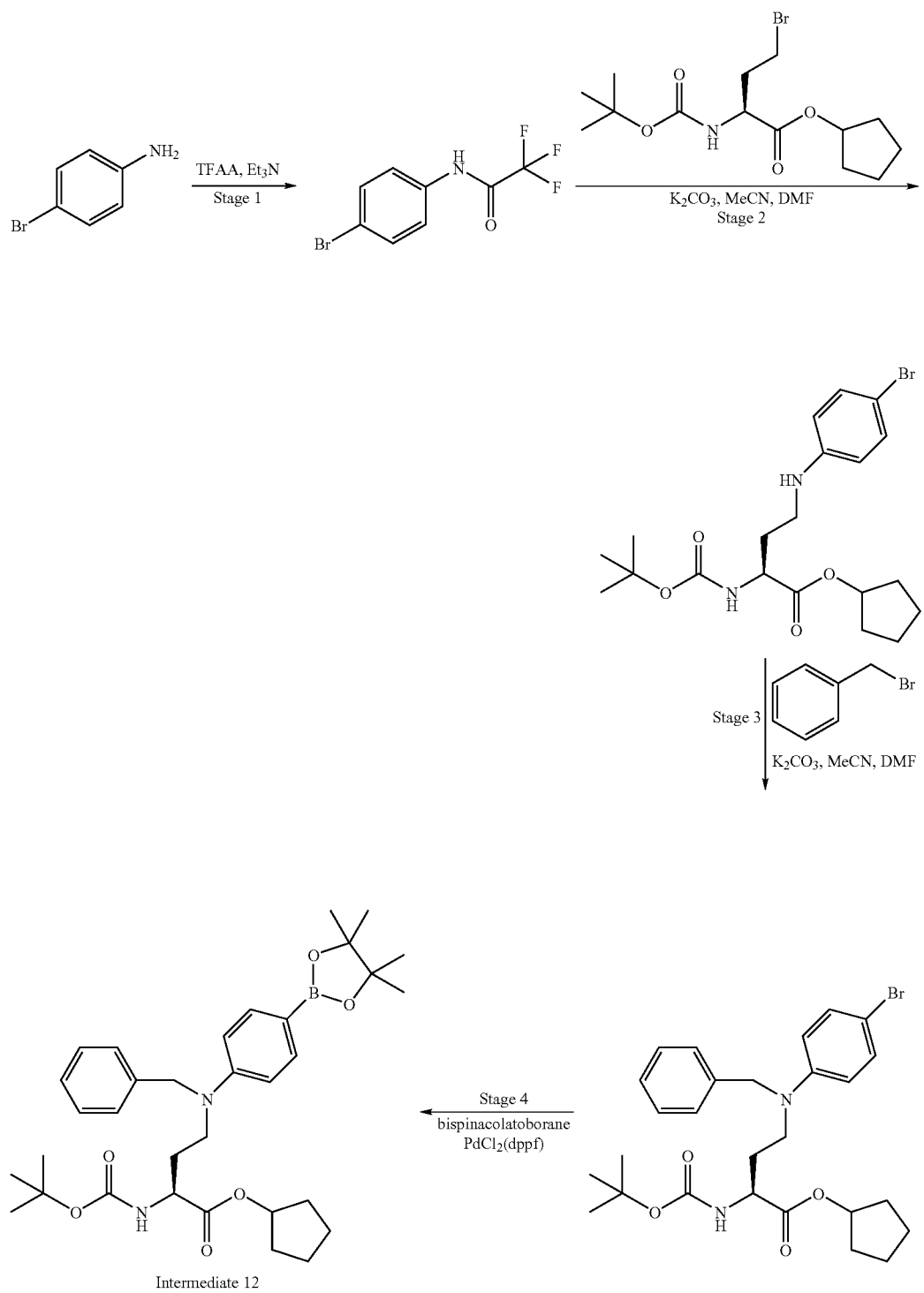

Intermediates

Intermediate 1
5-Bromo-2-(carbamoylamino)thiophene-3-carboxamide

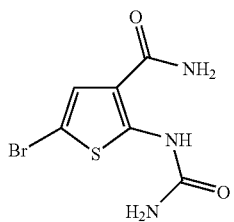

The synthesis of Intermediate 1 highlighted by Stages 1-4 in Scheme 1 is detailed within WO03104218.

Intermediate 2a Cyclopentyl N-(tert-butoxycarbonyl)-O-[4-(4,4,5,5-tetramethyl-1,3,2-dioxaborolan-2-yl)phenyl]-D-homoserinate

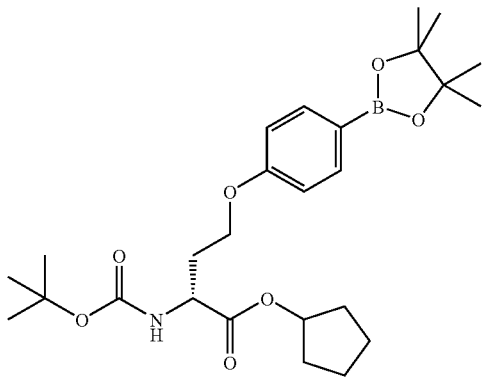

The synthesis of Intermediate 2a is detailed within Scheme 2 and full experimental details are shown below.

Stage 1—O[tert-Butyl(dimethyl)silyl]-D-homoserine

To a suspension of D-homoserine (1 g, 8.4 mmol) in acetonitrile (10 ml) at 0° C. was added 1,8-diazabicyclo[5.4.0]undec-7-ene (1.32 ml, 8.8 mmol, 1.05 eq). tert-Butyl-dimethylsilyl chloride (1.33 g, 8.8 mmol, 1.05 eq) was then added portionwise over 5 minutes and the reaction mixture allowed to warm to room temperature and stirred for 16 hrs. A white precipitate had formed which was filtered off and washed with acetonitrile before drying under vacuum. The title compound was isolated as a white solid (1.8 g, 92%).

$^1$H NMR (400 MHz, DMSO), δ: 7.5 (1H, br s), 3.7 (1H, m), 3.35 (4H, bm), 1.95 (1H, m), 1.70 (1H, m), 0.9 (9H, s), 0.1 (6H, s).

Stage 2—N-(tert-Butoxycarbonyl)-O-[tert-butyl(dimethyl)silyl]-D-homoserine

The suspension of O-[tert-Butyl(dimethyl)silyl]-D-homoserine (1.8 g, 7.7 mmol) in DCM (100 ml) at 0° C. was treated with triethylamine (2.15 ml, 15.4 mmol, 2 eq) and di-tert-butyl dicarbonate (1.77 g, 8.1 mmol, 1.05 eq). The reaction mixture was stirred at room temperature for 16 hours for complete reaction. The DCM was removed under reduced pressure and the mixture was treated with ethyl acetate/brine. The ethyl acetate layer was dried over magnesium sulphate and evaporated under reduced pressure. The crude product was taken forward without further purification (2.53 g, 99%).

$^1$H NMR (400 MHz, CDCl$_3$), δ: 7.5 (1H, br s), 5.85 (1H, d, J=6.5 Hz), 4.3 (1H, m), 3.75 (2H, m), 1.95 (2H, m), 1.40 (9H, s), 0.85 (9H, s), 0.1 (6H, s).

Stage 3—Cyclopentyl N-(tert-butoxycarbonyl)-O-[tert-butyl(dimethyl)silyl]-D-homoserinate To a solution of N-(tert-butoxycarbonyl)-O-[tert-butyl(dimethyl)silyl]-D-homoserine (2.53 g, 7.6 mmol) in DCM (50 ml) at 0° C. was added cyclopentanol (1.39 ml, 15.3 ml, 2 eq), EDC (1.61 g, 8.4 mmol, 1.1 eq) and DMAP (0.093 g, 0.76 mmol, 0.1 eq). The reaction mixture was stirred for 16 hours at room temperature before evaporation under reduced pressure. The crude residue was dissolved in ethyl acetate (100 ml) and washed with 1M HCl, 1M Na$_2$CO$_3$ and brine. The organic layer was then dried over magnesium sulphate and evaporated under reduced pressure. The product was purified by column chromatography using ethyl acetate/heptane (1:4) to give 2.24 g, 73% yield of title compound.

LCMS purity 100%, m/z 402.5 [M+H]$^+$, $^1$H NMR (400 MHz, CDCl$_3$), δ: 5.2 (1H, d, J=6.3 Hz), 5.15 (1H, m), 4.2 (1H, m), 3.6 (2H, m), 2.0 (1H, m), 1.95-1.55 (9H, bm), 1.4 (9H, s), 0.85 (9H, s), 0.1 (6H, s).

Stage 4—Cyclopentyl(2R)-4-hydroxy-2-[(tert-butoxycarbonyl)amino]butanoate

Cyclopentyl N-(tert-butoxycarbonyl)-O-[tert-butyl(dimethyl)silyl]-D-homoserinate (1.57 g, 3.9 mmol) was dissolved in acetic acid:THF:water (3:1:1, 100 ml). The reaction mixture was stirred at 30° C. for 16 hours for complete reaction. Ethyl acetate (200 ml) was added and washed with 1M Na$_2$CO$_3$, 1M HCl and brine. The ethyl acetate extracts were dried over magnesium sulphate and evaporated under reduced pressure to give the product as a clear oil which crystallised on standing (1.0 g, 95%).

LCMS purity 100%, m/z 310.3 [M+Na]$^+$, $^1$H NMR (400 MHz, CDCl$_3$), δ: 5.4 (1H, d, J=6.5 Hz), 5.2 (1H, m), 4.4 (1H, m), 3.65 (2H, m), 2.15 (1H, m), 1.9-1.55 (9H, bm), 1.45 (9H, s).

Stage 5—Cyclopentyl(2R)-4-bromo-2-[(tert-butoxycarbonyl)amino]butanoate

To a slurry of N-bromo succinimide (1.86 g, 10.4 mmol) in DCM (16.2 ml) was added a solution of triphenyl phosphine (2.56 g, 9.74 mmol) in DCM (7.2 ml). The solution was stirred for a further 5 minutes after addition. Pyridine (338 µl, 4.18 mmol) was added, followed by a solution of cyclopentyl (2R)-4-hydroxy-2-[(tert-butoxycarbonyl)amino]butanoate (1.0 g, 3.48 mmol) in DCM (8.8 ml). The solution was stirred for 18 hrs, concentrated in vacuo and the residual solvent azeotroped with toluene (3×16 ml). The residue was triturated with diethyl ether (10 ml) and ethyl acetate:heptane (1:9, 2×10 ml). The combined ether and heptane solutions was concentrated onto silica and purified by column chromatography using ethyl acetate/heptane (1:9-2:8) to provide 1.02 g (84% yield) of title compound.

$^1$H NMR (400 MHz, CDCl$_3$), δ: 5.3-5.05 (2H, m), 4.45-4.3 (1H, m), 3.45 (2H, t, J=7.3 Hz), 2.50-2.30 (1H, m), 2.25-2.10 (1H, m), 1.95-1.60 (8H, b m), 1.47 (9H, s).

Stage 6—Cyclopentyl O-(4-bromophenyl)-D-homoserinate

A solution of 4-bromophenol (0.593 g, 3.43 mmol) in DMF (5 ml) was cooled to 0° C. with an ice bath and NaH (0.137 g, 3.43 mmol) was added in a single portion. The reaction was allowed to warm to RT, sonicated briefly and cooled down again to 0° C. A solution of cyclopentyl(2R)-4-bromo-2-[(tert-butoxycarbonyl)amino]butanoate (1.2 g, 3.43 mmol) in THF (10 ml) was then added dropwise, and the reaction allowed to warm to room temperature. After 1 hr the reaction was heated to 50° C. and monitored by TLC for complete reaction. After 4 hrs, the reaction appeared to be complete and was allowed to cool to room temperature and poured onto a mixture of EtOAc and saturated NaHCO$_3$. The organic layer was collected, washed with 3 portions of water, brine and then dried (MgSO$_4$), filtered and evaporated in vacuo. The residue still contained small amounts of 4-bromophenol which was removed by scavenging with MP-carbonate (2 g) in DCM (7 ml), and the filtrate was evaporated to give the product as a white solid (1.2 g, 79%). m/z 443 [M+H]$^+$.

Stage 7—Cyclopentyl N-(tert-butoxycarbonyl)-O-[4-(4,4,5,5-tetramethyl-1,3,2-dioxaborolan-2-yl)phenyl]-D-homoserinate A mixture of cyclopentyl O-(4-bromophenyl)-D-homoserinate (1.2 g, 2.71 mmol), KOAc (0.346 g, 3.53 mmol), Bis[pinacolato]diboron (1.378 g, 5.43 mmol) and PdCl$_2$(dppf) (0.198 g, 0.271 mmol) in DMSO was heated under a nitrogen atmosphere at 65° C. and monitored by LC-MS for the formation of the product. After 1 hr the reaction was complete, hence the reaction mixture was cooled to room temperature and poured onto a mixture of EtOAc and 1M HCl. The layers were separated, the organic layer washed with water and brine, dried over magnesium sulphate, filtered and evaporated under reduced pressure. The residue was subjected to column chromatography eluting with 5% to 10% EtOAc in hexanes (0.65 g, 49%). m/z 490 [M+H]$^+$.

Intermediate 2b Cyclopentyl N-(tert-butoxycarbonyl)-O-[4-(4,4,5,5-tetramethyl-1,3,2-dioxaborolan-2-yl)phenyl]-L-homoserinate

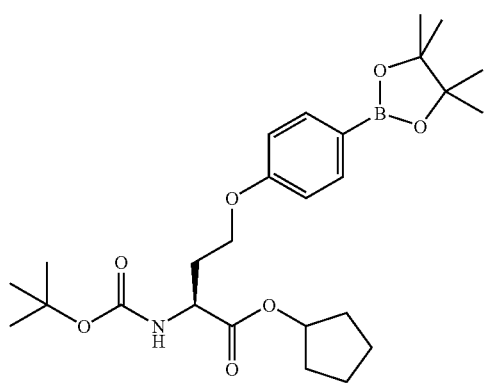

Synthesised via analogous methods to Intermediate 2a, using L-Homoserine at Stage 1 of Scheme 2. LCMS: m/z 490 [M+H]$^+$.

Intermediate 3a Cyclopentyl N-(tert-butoxycarbonyl)-5-[4-(4,4,5,5-tetramethyl-1,3,2-dioxaborolan-2-yl)phenoxy]-L-norvalinate

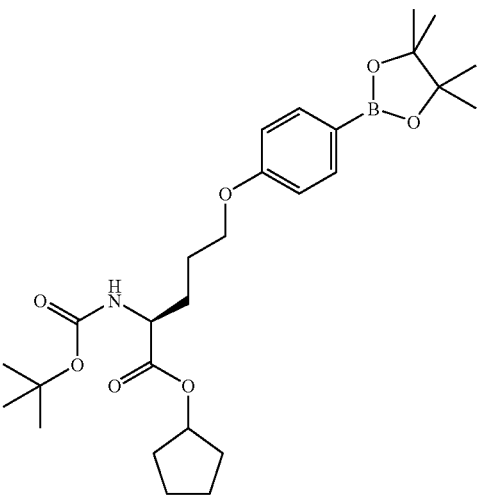

The synthesis of Intermediate 3a is detailed within Scheme 3 and full experimental details are shown below.

Stage 1: (S)-2-tert-Butoxycarbonylamino-pentanedioic acid 5-benzyl ester 1-cyclopentyl ester To a solution of Boc-L-Glu(OBzl)-OH (15 g, 44.5 mmol) in dichloromethane (220 ml) in an ice-bath, was added cyclopentanol (4.8 ml, 53.3 mmol, 1.2 eq), EDC (9.4 g, 48.9 mmol, 1.1 eq) and DMAP (543 mg, 4.4 mmol, 0.1 eq). The reaction mixture was allowed to warm to room temperature and stirred for 12 hours for complete reaction. The reaction mixture was diluted with DCM (200 ml) and washed with 1M HCl, 1M Na$_2$CO$_3$ and brine. The organic layer was then dried over magnesium sulphate and evaporated under reduced pressure. The product was purified by column chromatography using ethyl acetate/heptane (1:4) to give 12.4 g, 69% yield of title compound as a white solid.

$^1$H NMR (300 MHz, CDCl$_3$), δ: 7.38 (5H, m), 5.70 (1H, m), 5.10 (2H, s), 5.05 (1H, m), 4.25 (1H, m), 2.47 (2H, m), 2.15 (1H, m), 1.95-1.55 (9H, bm), 1.47 (9H, s).

Stage 2: (S)-2-tert-Butoxycarbonylamino-pentanedioic acid 1-cyclopentyl ester (S)-2-tert-Butoxycarbonylamino-pentanedioic acid 5-benzyl ester 1-cyclopentyl ester (12.4 g, 30.5 mmol) was dissolved in EtOAc (200 ml) and purged with nitrogen before addition of 20% Pd(OH)$_2$ on carbon catalyst (1.3 g). The reaction flask was then purged with hydrogen gas for a period of 5 minutes before leaving under a balloon of hydrogen for 5 hours for complete reaction. The catalyst was removed by filtration, washing with 50 ml EtOAc and the combined mother liquors were evaporated under reduced pressure. The title compound was isolated as a clear oil (7.73 g, 85%) and required no further purification.

$^1$H NMR (300 MHz, CDCl$_3$), δ: 10.0 (1H, br s), 5.70 (2H, m), 4.28 (1H, m), 2.47 (2H, m), 2.15 (1H, m), 1.95-1.55 (9H, bm), 1.47 (9H, s).

Stage 3:
(S)-2-tert-Butoxycarbonylamino-5-hydroxy-pentanoic acid cyclopentyl ester Ethyl chloroformate (2.45 ml, 25.6 mmol, 1.2 eq) was added at −20° C. to a stirred solution of (S)-2-tert-butoxycarbonylamino-pentanedioic acid 1-cyclopentyl ester (6.73 g, 21.4 mmol) and N-methyl morpholine (3.05 ml, 27.8 mmol, 1.3 eq) in THF (50 ml). The reaction mixture became very thick with precipitation of a white solid. The reaction was therefore diluted further with THF (100 ml) to aid mixing and left stirring at −20° C. for 2 hours. The precipitated mass was filtered off and the filtrate was added over a period of 20 minutes to a solution of sodium borohydride (2.43 g, 64.1 mmol, 3 eq) in THF (20 ml) and water (5 ml) at 0° C. The reaction mixture was allowed to stir to room temperature and left for 4 hours for complete reaction. The mixture was acidified to pH 5 with 1M HCl and the THF removed under reduced pressure. The aqueous solution was extracted with EtOAc (3×100 ml) and dried over magnesium sulphate. The product was purified by column chromatography (DCM-5% MeOH/DCM) and isolated as a clear oil (5.0 g, 78%).

$^1$H NMR (300 MHz, CDCl$_3$), δ: 5.20 (2H, m), 4.25 (1H, m), 3.65 (2H, m), 2.00-1.57 (12H, bm), 1.47 (9H, s).

Stage 4—(S)-5-Bromo-2-tert-butoxycarbonylaminopentanoic acid cyclopentyl ester

To a slurry of N-bromo succinimide (3.54 g, 19.9 mmol, 3 eq) in DCM (30 ml) was added a solution of triphenyl phosphine (4.87 g, 18.8 mmol, 2.8 eq) in DCM (15 ml). The solution was stirred for a further 5 minutes before addition of pyridine (644 μl, 7.96 mmol, 1.2 eq) and a solution of (S)-2-tert-butoxycarbonylamino-5-hydroxy-pentanoic acid cyclopentyl ester (2.0 g, 6.64 mmol) in DCM (20 ml). The solution was stirred for 18 hrs, concentrated in vacuo and the residual solvent azeotroped with toluene (3×30 ml). The residue was triturated with diethyl ether (30 ml) and ethyl acetate:heptane (1:9, 2×30 ml). The combined ether and ethyl acetate/heptane solutions was concentrated onto silica and purified by column chromatography using ethyl acetate/heptane (1:9-2:8) to provide 1.34 g (55% yield) of title compound as a clear oil.

$^1$H NMR (300 MHz, CDCl$_3$), δ: 5.25 (1H, m), 5.05 (1H, bd), 3.45 (2H, m), 2.00-1.55 (12H, bm), 1.45 (9H, s).

Stage 5: Cyclopentyl 5-(4-bromophenoxy)-N-(tert-butoxycarbonyl)-L-norvalinate

To a solution of 4-bromophenol (261 mg, 1.510 mmol) in acetonitrile (2 ml) under nitrogen, was added BEMP (397 μl, 1.373 mmol). The mixture was stirred at 50° C. for 30 minutes before being cooled to room temperature and (S)-5-bromo-2-tert-butoxycarbonylamino-pentanoic acid cyclopentyl ester (500 mg, 1.373 mmol) added as a solution in acetonitrile (2 ml). The reaction was heated at 50° C. for a further 1 hour and then the mixture was analysed by LCMS. The reaction was poured onto 2M Na$_2$CO$_3$ (100 ml) and extracted with EtOAc (2×100 ml). The combined organic layers were washed with 2M Na$_2$CO$_3$ (3×100 ml) and brine (100 ml), dried over magnesium sulphate, filtered and concentrated in vacuo to afford a colourless oil. MP-carbonate (1.0 g) was added to a solution of the crude product in dichloromethane (3.4 ml) and the solution was left overnight at room temperature. LCMS indicated complete removal of 4-bromophenol and so the reaction was filtered to remove the MP-carbonate and the resin was washed with DCM (2×50 ml). The filtrate was concentrated to afford the crude product which was purified by column chromatography eluting with 5% EtOAc in iso-hexane. Yield of title compound=435 mg, 0.953 mmol, 69.4% yield. m/z 456 and 458 [M+H]$^+$.

Stage 6: Cyclopentyl N-(tert-butoxycarbonyl)-5-[4-(4,4,5,5-tetramethyl-1,3,2-dioxaborolan-2-yl)phenoxy]-L-norvalinate DMSO (1.6 ml) was added to a vial containing cyclopentyl 5-(4-bromophenoxy)-N-(tert-butoxycarbonyl)-L-norvalinate (430 mg, 0.942 mmol), Bis[pinacolato]diboron (479 mg, 1.884 mmol), potassium acetate (120 mg, 1.225 mmol) and PdCl$_2$(dppf) (77 mg, 0.094 mmol) under nitrogen. Nitrogen was bubbled through the solution for approximately five minutes then the reaction was heated to 65° C. overnight. LCMS indicated completion of reaction and so the reaction was cooled to room temperature and partitioned between ether and water. The layers were separated and the organic layer was washed with water and brine, then dried over magnesium sulphate and concentrated in vacuo. Purification was achieved by column chromatography eluting with 10% EtOAc in iso-hexane. Yield of title compound=380 mg, 0.755 mmol, 80% yield. m/z 504 [M+H]$^+$.

Intermediate 3b Cyclopentyl N-(tert-butoxycarbonyl)-5-[4-(4,4,5,5-tetramethyl-1,3,2-dioxaborolan-2-yl)phenoxy]-D-norvalinate

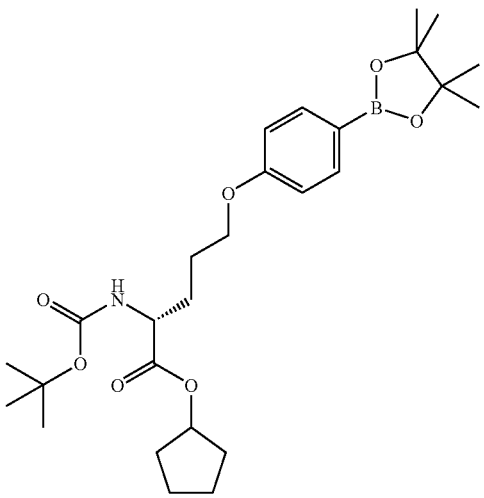

Synthesised via analogous methods to Intermediate 3a, using Boc-D-Glu(OBzl)-OH at Stage 1 of Scheme 3. m/z 504 [M+H]+.

Intermediate 4a Cyclopentyl N-(tert-butoxycarbonyl)-O-[3-methyl-4-(4,4,5,5-tetramethyl-1,3,2-dioxaborolan-2-yl)phenyl]-L-homoserinate

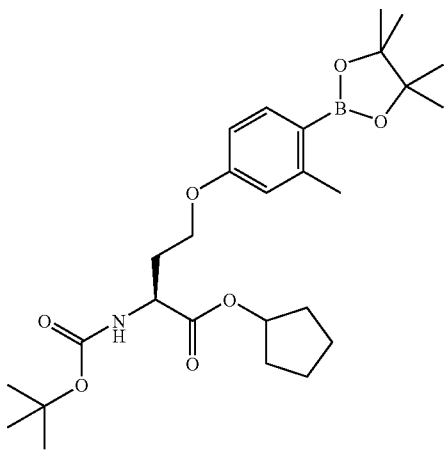

Synthesised by analogous methods to Intermediate 2b, using 4-bromo-3-methyl-phenol at Stage 6 of Scheme 2. m/z 504 [M+H]+.

Intermediate 4b Cyclopentyl N-(tert-butoxycarbonyl)-O-[2-methyl-4-(4,4,5,5-tetramethyl-1,3,2-dioxaborolan-2-yl)phenyl]-L-homoserinate

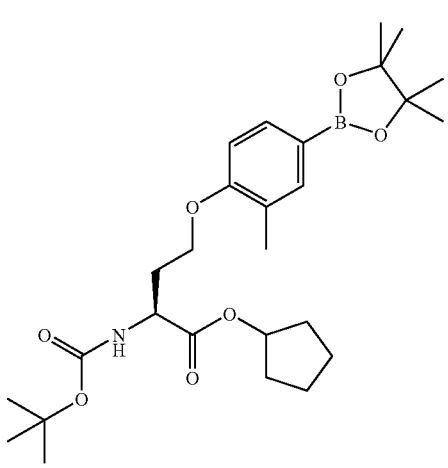

Synthesised by analogous methods to Intermediate 2b, using 4-bromo-2-methyl-phenol at Stage 6 of Scheme 2. m/z 504 [M+H]+.

Intermediate 4c Cyclopentyl N-(tert-butoxycarbonyl)-O-[3-chloro-4-(4,4,5,5-tetramethyl-1,3,2-dioxaborolan-2-yl)phenyl]-L-homoserinate

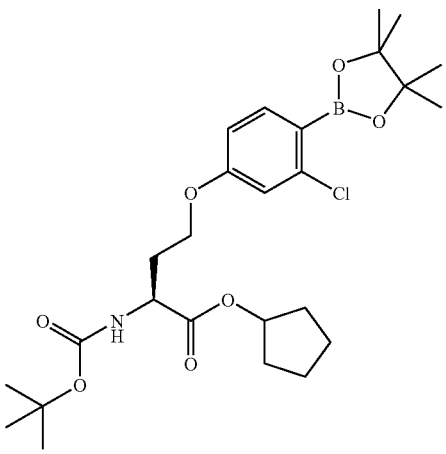

Synthesised by analogous methods to Intermediate 2b, using 4-bromo-3-chloro-phenol at Stage 6 of Scheme 2. m/z 524 [M+H]+.

Intermediate 4d Cyclopentyl N-(tert-butoxycarbonyl)-O-[2-chloro-4-(4,4,5,5-tetramethyl-1,3,2-dioxaborolan-2-yl)phenyl]-L-homoserinate

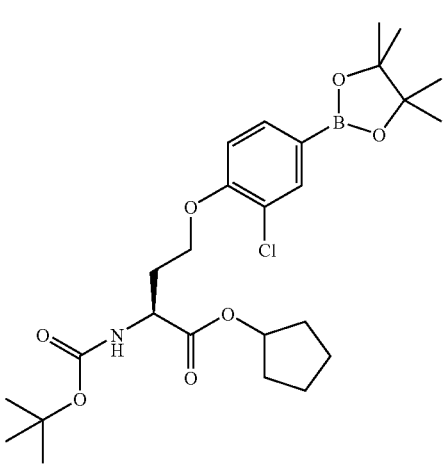

Synthesised by analogous methods to Intermediate 2b, using 4-bromo-2-chloro-phenol at Stage 6 of Scheme 2. m/z 524 [M+H]⁺.

Intermediate 5a Cyclopentyl(2S,4E)-2-[(tert-butoxycarbonyl)amino]-5-[4-(4,4,5,5-tetramethyl-1,3,2-dioxaborolan-2-yl)phenyl]pent-4-enoate

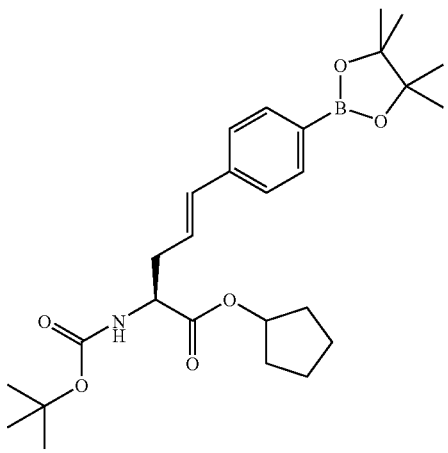

The synthesis of Intermediate 5a is detailed within Scheme 4 and full experimental details are shown below.

Stage 1: Cyclopentyl(2S)-2-[(tert-butoxycarbonyl)amino]pent-4-enoate

To a stirred solution of DMAP (0.057 g, 0.465 mmol) in DCM (20 ml) was added EDC (0.980 g, 5.11 mmol). A solution of Boc-L-allylglycine (1.0 g, 4.65 mmol) in DCM (5 ml) was added and the mixture stirred for 20 minutes at RT. Cyclopentanol (0.506 ml, 5.58 mmol) was then added and the mixture stirred overnight at RT for complete reaction. After concentration of the reaction solvent in vacuo, the residue was subjected to column chromatography eluting with 6% EtOAc in hexanes. Yield=0.907 g, 3.20 mmol, 68.9% yield. m/z 284 [M+H]⁺.

Stage 2: Cyclopentyl(2S,4E)-5-(4-bromophenyl)-2-[(tert-butoxycarbonyl)amino]pent-4-enoate A solution of cyclopentyl(2S)-2-[(tert-butoxycarbonyl)amino]pent-4-enoate (0.88 g, 3.11 mmol), 1-bromo-4-iodobenzene (0.966 g, 3.42 mmol), TBAI (1.262 g, 3.42 mmol) and NaHCO₃ (0.783 g, 9.32 mmol) in acetonitrile (10 ml) was purged with N₂ and palladium acetate (0.070 g, 0.311 mmol) was added. The reaction was then heated at 70° C. overnight. LCMS showed incomplete conversion and so the reaction was purged with nitrogen again and a further 0.05 eq (35 mg) of Pd(OAc)₂, 0.25 eq (460 mg) of TBAI and 0.25 eq of NaHCO₃ (65 mg) was added and stirred for another 24 hr at 70° C. After cooling to room temperature, the solvent was removed under reduced pressure. The crude residue was absorbed onto silica and purified by column chromatography eluting with 10% EtOAc in iso-hexane. Yield=715 mg, 1.631 mmol, 52.5% yield. LCMS purity>90%: m/z 438 and 440 [M+H]⁺.

Stage 3: Cyclopentyl(2S,4E)-2-[(tert-butoxycarbonyl)amino]-5-[4-(4,4,5,5-tetramethyl-1,3,2-dioxaborolan-2-yl)phenyl]pent-4-enoate DMSO (4 ml) was added to cyclopentyl(2S,4E)-5-(4-bromophenyl)-2-[(tert-butoxycarbonyl)amino]pent-4-enoate (700 mg, 1.597 mmol), Bis[pinacolato]diboron (811 mg, 3.19 mmol), potassium acetate (204 mg, 2.076 mmol) and PdCl₂(dppf) (130 mg, 0.160 mmol) under a nitrogen atmosphere. Nitrogen was bubbled through for approximately 5 minutes and then the reaction was heated at 65° C. overnight. LCMS indicated completion conversion and so the reaction was cooled to room temperature and partitioned between diethyl ether and water. The layers were separated and the organic layer was washed with water and brine, then dried over magnesium sulphate and concentrated in vacuo. Purification was achieved by column chromatography eluting with 6-10% EtOAc in iso-hexane. Yield=315 mg, 0.649 mmol, 40.6% yield. LCMS purity>90%: m/z 486 [M+H]⁺.

Intermediate 5b Cyclopentyl(2R,4E)-2-[(tert-butoxycarbonyl)amino]-5-[4-(4,4,5,5-tetramethyl-1,3,2-dioxaborolan-2-yl)phenyl]pent-4-enoate

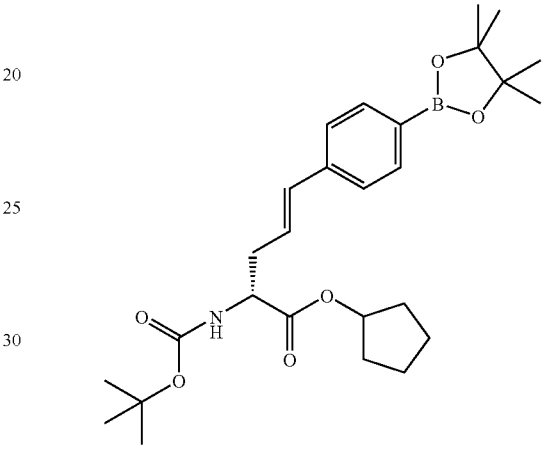

Synthesised via analogous methods to Intermediate 5a, using Boc-D-allylglycine at Stage 1 of Scheme 4. LCMS: m/z 486 [M+H]⁺.

Intermediate 5c tert-Butyl(2S,4E)-2-amino]-5-[4-(4,4,5,5-tetramethyl-1,3,2-dioxaborolan-2-yl)phenyl]pent-4-enoate

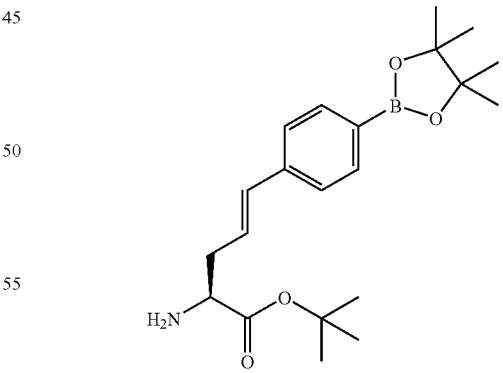

The synthesis of Intermediate 5c is detailed below.

Stage 1: Fmoc-L-Allylglycine tert-butyl ester

To a solution of Fmoc-L-Allylglycine (4 g, 11.86 mmol) in dichloromethane (120 ml) was added a solution of tert-butyl-2,2,2-trichloroacetimidate (4.24 ml, 23.71 mmol) in cyclohexane (6 ml). Boron trifluoride etherate (1.502 ml, 11.86 mmol) was then added and the reaction mixture left to stir at RT overnight. LCMS indicated some starting material remained so a further 0.5 eq of boron trifluoride etherate and 0.5 eq of tert-butyl-2,2,2-trichloroacetimidate were added to the reaction mixture. After stirring for 4 hours, reaction was complete. To the reaction mixture was added saturated NaHCO$_3$ solution (100 ml). The organic layer was separated and the cloudy aqueous layer was extracted with a further two portions of dichloromethane (2×30 ml). Combined organics were washed sequentially with saturated NaHCO$_3$ solution and brine before being dried (MgSO$_4$) and concentrated in vacuo to afford an opaque oil. The crude product was purified by column chromatography, eluting with 5% ethyl acetate in isohexane. Yield=3.4 g, 8.64 mmol, 58%.

Stages 2 and 3 follow similar experimental details to Stages 2 and 3 in the synthesis of Intermediate 5a. The 9-fluorenyl-methoxycarbonyl protecting group is conveniently removed using the reaction conditions employed in Stage 3. LCMS: m/z 374 [M+H]$^+$.

Intermediate 6a Cyclopentyl N-(tert-butoxycarbonyl)-5-{4-[4-carbamoyl-5-(carbamoylamino)-2-thienyl]phenyl}-L-norvalinate

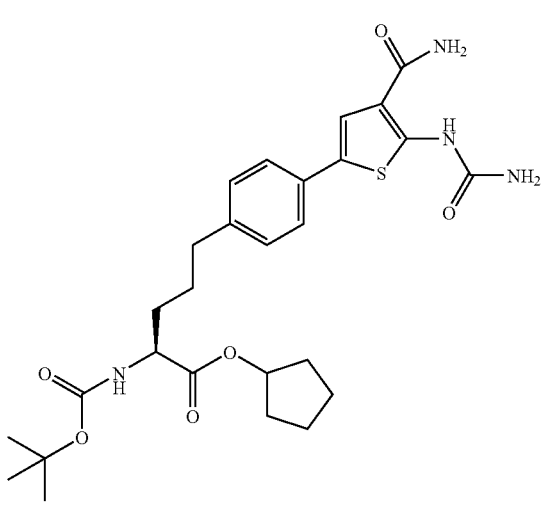

The synthesis of Intermediate 6a is detailed within Scheme 5 and full experimental details are shown below.

Stage 1: Cyclopentyl(2S,4E)-2-[(tert-butoxycarbonyl)amino]-5-{4-[4-carbamoyl-5-(carbamoylamino)-2-thienyl]phenyl}pent-4-enoate To a mixture of cyclopentyl(2S,4E)-2-[(tert-butoxycarbonyl)amino]-5-[4-(4,4,5,5-tetramethyl-1,3,2-dioxaborolan-2-yl)phenyl]pent-4-enoate (Intermediate 5a) (810 mg, 1.669 mmol), Intermediate 1 (401 mg, 1.517 mmol) and tetrakis(triphenylphosphine) Pd catalyst (175 mg, 0.152 mmol) was added DME (8 ml) followed by a solution of sat. NaHCO$_3$ (3 ml). The mixture was placed in a preheated oil bath at 80° C. After 4 hrs the reaction was judged to be complete by LCMS. The mixture was cooled to RT, absorbed onto silica and subjected to column chromatography eluting with 5% MeOH in DCM. Yield=0.5 g, 0.857 mmol, 56.5% yield. LCMS purity 93%: m/z 543 [M+H]$^+$, 541 [M–H]$^+$.

Stage 2: Cyclopentyl N-(tert-butoxycarbonyl)-5-{4-[4-carbamoyl-5-(carbamoylamino)-2-thienyl]phenyl}-L-norvalinate Hydrogen gas was bubbled through a suspension of Wilkinson's catalyst (767 mg, 0.829 mmol) in IPA (10 ml) and toluene (5 ml). After 5 minutes, a solution of cyclopentyl (2S,4E)-2-[(tert-butoxycarbonyl)amino]-5-{4-[4-carbamoyl-5-(carbamoylamino)-2-thienyl]phenyl}pent-4-enoate (300 mg, 0.553 mmol) in IPA (10 ml) was added. The mixture was kept under an atmosphere of hydrogen and placed in a preheated oil bath at 80° C. After 4 hrs the reaction was judged to be complete by LC-MS. The mixture was filtered whilst still hot and the filtrate evaporated in vacuo. The residue was subjected to column chromatography eluting with 4% MeOH in DCM. Yield=120 mg, 0.198 mmol, 36% yield. LCMS purity 90%: m/z 543 [M–H]$^+$.

Intermediate 6b Cyclopentyl N-(tert-butoxycarbonyl)-5-{4-[4-carbamoyl-5-(carbamoylamino)-2-thienyl]phenyl}-D-norvalinate

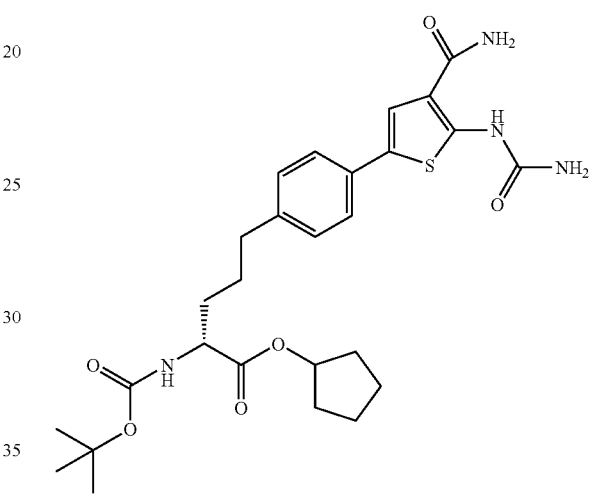

Synthesised via analogous methods to Intermediate 6a, using Intermediate 5b at Stage 1 of Scheme 5. m/z 545 [M+H]$^+$.

Intermediate 7a Cyclopentyl(2S,4E)-2-[(tert-butoxycarbonyl)amino]-5-[3-chloro-4-(4,4,5,5-tetramethyl-1,3,2-dioxaborolan-2-yl)phenyl]pent-4-enoate

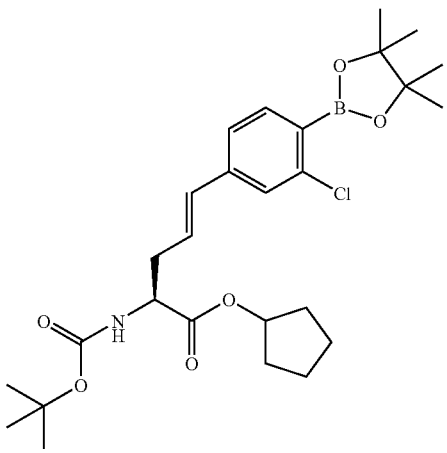

Synthesised by analogous methods to Intermediate 5a, using 4-bromo-3-chloro-iodobenzene at Stage 2 of Scheme 4. m/z 520 [M+H]+.

Intermediate 7b Cyclopentyl(2S,4E)-2-[(tert-butoxycarbonyl)amino]-5-[2-methyl-4-(4,4,5,5-tetramethyl-1,3,2-dioxaborolan-2-yl)phenyl]pent-4-enoate

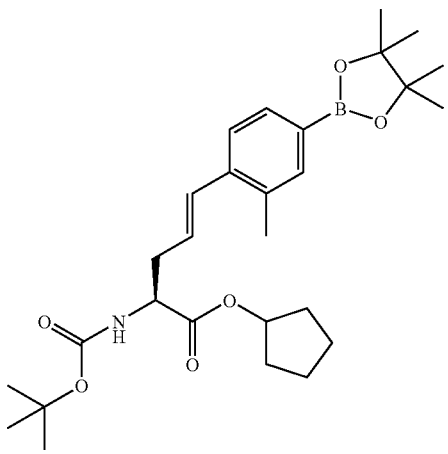

Synthesised by analogous methods to Intermediate 5a, using 4-bromo-2-methyl-iodobenzene at Stage 2 of Scheme 4. m/z 500 [M+H]+.

Intermediate 8 Cyclopentyl(2S)-2-[(tert-butoxycarbonyl)amino]-5-[4-(4,4,5,5-tetramethyl-1,3,2-dioxaborolan-2-yl)phenyl]pent-4-ynoate

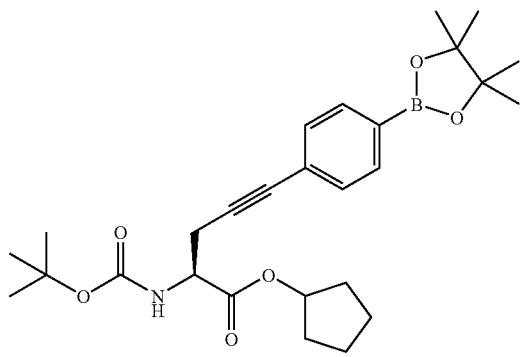

The synthesis of Intermediate 8 is detailed within Scheme 6 and full experimental details are shown below.

Stage 1: Cyclopentyl(2S)-2-[(tert-butoxycarbonyl)amino]pent-4-ynoate

To a solution of Boc-L-propargyl glycine (5 g, 23.45 mmol) in DCM (100 ml) was added cyclopentanol (3.03 g, 35.2 mmol), EDC (4.93 g, 25.8 mmol) and DMAP (0.286 g, 2.345 mmol). The mixture was stirred overnight at RT. The solvent was removed under reduced pressure and the residue was subjected to column chromatography eluting with 7 to 12% EtOAc in hexanes. Yield=5.5 g, 19.55 mmol, 83% yield.

Stage 2: Cyclopentyl(2S)-5-(4-bromophenyl)-2-[(tert-butoxycarbonyl)amino]pent-4-ynoate To a mixture of cyclopentyl(2S)-2-[(tert-butoxycarbonyl)amino]pent-4-ynoate (2.45 g, 8.72 mmol) and 4-iodo-bromobenzene (2.96 g, 10.46 mmol) in diethyl ether (4 ml) was added copper iodide (0.166 g, 0.872 mmol) and PdCl$_2$(PPh$_3$)$_2$ (0.306 g, 0.436 mmol). Diethylamine (5.43 ml, 52.3 mmol) was then added and the mixture stirred at RT. After 2 hrs, LCMS showed complete reaction. The mixture was poured onto water and extracted with diethyl ether. The combined organic layers were washed with water and brine, dried over magnesium sulphate, filtered and evaporated in vacuo. The crude residue was subjected to column chromatography eluting with 5 to 10% EtOAc in hexanes. Yield=2.9 g, 6.51 mmol, 75% yield. LCMS purity 98%: m/z 437 [M+H]+.

Stage 3: Cyclopentyl(2S)-2-[(tert-butoxycarbonyl)amino]-5-[4-(4,4,5,5-tetramethyl-1,3,2-dioxaborolan-2-yl)phenyl]pent-4-ynoate To a mixture of cyclopentyl(2S)-5-(4-bromophenyl)-2-[(tert-butoxycarbonyl)amino]pent-4-ynoate (2.9 g, 6.65 mmol), Bis[pinacolato]diboron (2.025 g, 7.98 mmol), PdCl$_2$(dppf) (0.246 g, 0.332 mmol) and potassium acetate (0.978 g, 9.97 mmol) was added DMSO (10 ml). The mixture was purged with nitrogen and placed in a preheated oil bath at 80° C. for 12 hrs. The mixture was poured onto water and extracted with diethyl ether. The combined ether extracts were washed with water (×3) and brine (×2), dried over magnesium sulphate, filtered and evaporated in vacuo. The residue was subjected to column chromatography eluting with 5 to 10% EtOAc in hexanes. Yield=2.1 g, 3.69 mmol, 55.6% yield. LCMS purity 85%: m/z 484 [M+H]+.

Intermediate 9 Cyclopentyl N-(tert-butoxycarbonyl)-4-(4,4,5,5-tetramethyl-1,3,2-dioxaborolan-2-yl)-L-phenylalaninate

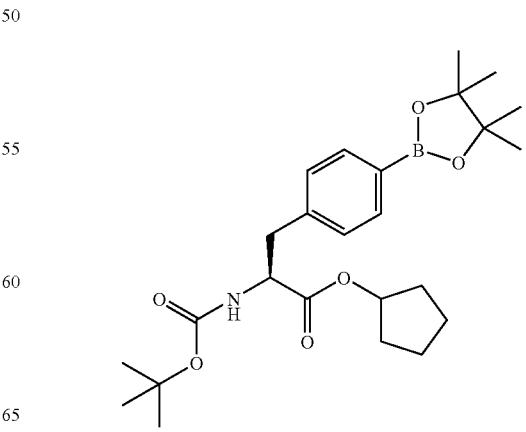

The synthesis of Intermediate 9 is detailed within Scheme 7 and follows analogous experimental details already described above. m/z 460 [M+H]+.

Intermediate 10 Cyclopentyl N-(tert-butoxycarbonyl)-O-[4-(4,4,5,5-tetramethyl-1,3,2-dioxaborolan-2-yl)benzyl]-L-homoserinate

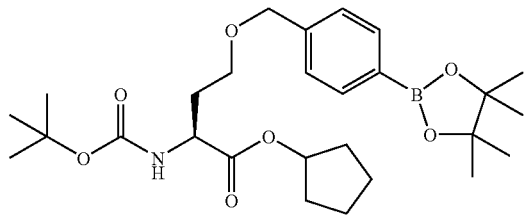

The synthesis of Intermediate 10 is detailed within Scheme 8 and follows experimental details shown below.

Stage 1: O-(4-bromobenzyl)-N-(tert-butoxycarbonyl)-L-homoserine

To a flask containing Boc-L-homoserine (5.181 g, 23.63 mmol)) in THF (50 ml) was added sodium hydride (2.93 g, 73.3 mmol) and left stirring at 0° C. for 30 minutes. The reaction mixture was warmed to RT and left for 2 hrs. 4-bromo-benzylbromide (11.81 g, 47.3 mmol) was then added as a THF solution (15 ml) dropwise. The reaction was left at RT for 20 hrs. The reaction was quenched with MeOH and the solvent removed in vacuo. The residue was dissolved in water and washed with Et$_2$O. The aqueous layer was acidified with 2M HCl and exhaustively extracted with EtOAc. The organic layer was washed with water and brine, dried over magnesium sulphate and concentrated in vacuo. The oily residue (11 g) was purified by column chromatography eluting with 50-100% EtOAc in hexanes and flushed with 10-50% MeOH in EtOAc. Yield=927 mg, 2.388 mmol, 10% yield as a viscous oil. m/z 386/388 [M−H]+.

Stages 2 and 3 are described in analogous experimental details shown above. m/z 504 [M+H]+.

Intermediate 11 Cyclopentyl(2S,4Z)-2-[(tert-butoxycarbonyl)amino]-5-[4-(4,4,5,5-tetramethyl-1,3,2-dioxaborolan-2-yl)phenyl]pent-4-enoate

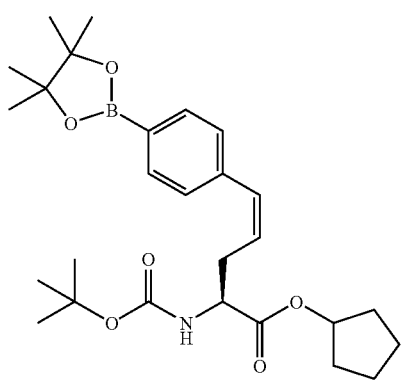

The synthesis of Intermediate 11 is detailed within Scheme 6 and follows experimental details shown below.

Stage 4: Cyclopentyl(2S,4Z)-5-(4-bromophenyl)-2-[(tert-butoxycarbonyl)amino]pent-4-enoate A mixture of cyclopentyl(2S)-5-(4-bromophenyl)-2-[(tert-butoxycarbonyl)amino]pent-4-ynoate (750 mg, 1.719 mmol), quinoline (41 µl, 3.44 mmol), 5% Pd on CaCO$_3$ (500 mg) was purged with nitrogen. EtOH (60 ml) was added and the mixture was stirred under an atmosphere of H$_2$ at room temperature for 21 hrs. Because of incomplete reaction, the mixture was filtered through Celite, treated with fresh catalyst (500 mg) and stirred under an atmosphere of H$_2$ at room temp for a further 18 hrs. The mixture was filtered through Celite and the filtrate evaporated in vacuo to afford the crude product as a colourless oil. Column purification using 5% EtOAc/isohexane afforded the product (640 mg, 1.416 mmol, 82% yield) as a clear colourless oil. LCMS purity 97%: m/z 439 [M+H]+. $^1$H NMR showed 8 wt % trans-alkene.

Stage 5 is described in analogous experimental details shown above. m/z 486 [M+H]+.

Intermediate 12 Cyclopentyl(2S)-4-{benzyl[4-(4,4,5,5-tetramethyl-1,3,2-dioxaborolan-2-yl)phenyl]amino}-2-[(tert-butoxycarbonyl)amino]butanoate

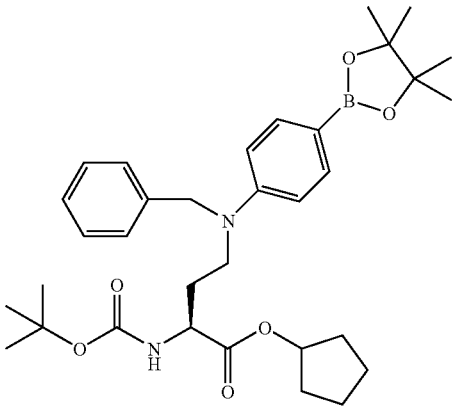

The synthesis of Intermediate 12 is detailed within Scheme 10 and full experimental details are shown below.

Stage 1: N-(4-Bromophenyl)-2,2,2-trifluoroacetamide

To an ice cold solution of 4-bromoaniline (3 g, 17.44 mmol) in DCM (40 ml) was added triethylamine (3.53 g, 34.9 mmol) followed by trifluoroacetic anhydride (2.67 ml, 19.18 mmol) by dropwise addition. After stirring at this temperature for 30 minutes, the reaction was allowed to warm to RT and stirred for a further 1 hr. The mixture was then poured onto sat. NaHCO$_3$, the layers separated and the aqueous layer extracted with DCM. The combined organics extracts were washed with water and brine, then dried (MgSO$_4$), filtered and evaporated in vacuo to give the product as an off-white solid (4.6 g, 17 mmol, 98% yield). LCMS purity 95%: m/z 269 [M+H]+.

Stage 2: Cyclopentyl(2S)-4-[(4-bromophenyl) amino]-2-[(tert-butoxycarbonyl)amino]butanoate Acetonitrile (40 ml) was added to a mixture of N-(4-bromophenyl)-2,2,2-trifluoroacetamide (1.3 g, 3.71 mmol), cyclopentyl(2S)-4-bromo-2-[(tert-butoxycarbonyl)amino] butanoate (0.904 g, 3.37 mmol) and K₂CO₃ (0.933 g, 6.75 mmol). The resulting suspension was heated to 60° C., DMF added (2 ml) and monitored for the formation of the product. After 6 days, the reaction was not complete; however the reaction was worked up to isolate any product formed. The solvent was evaporated, the residue dissolved in a mixture of water and EtOAc and the layers separated. The aqueous was extracted with a further portion of EtOAc and the combined organics, dried (MgSO₄), filtered and evaporated in vacuo to give a yellow oil (~1.8 g). This was subjected to column chromatography eluting with 10 to 15% EtOAc in hexanes to give the title compound as a colourless oil (660 mg, 1.5 mmol, 44% yield). LCMS purity 95%: m/z 442 [M+H]+.

Stage 3: Cyclopentyl(2S)-4-[benzyl(4-bromophenyl) amino]-2-[(tert-butoxycarbonyl)amino]butanoate To a mixture of cyclopentyl(2S)-4-[(4-bromophenyl) amino]-2-[(tert-butoxycarbonyl)amino]butanoate (0.66 g, 1.495 mmol), benzyl bromide (1.023 g, 5.98 mmol) and K₂CO₃ (0.620 g, 4.49 mmol) was added MeCN (15 ml) and DMF (1 ml). The suspension was heated overnight at 60° C. The reaction was then poured onto a mixture of water and EtOAc, the layers separated and the aqueous layer extracted with EtOAc. The combined organics were washed with water and brine, then dried (MgSO₄), filtered and evaporated in vacuo to give an oil (~1.5 g) which was subjected to column chromatography eluting with 5 to 10% EtOAc in hexanes to give the product (550 mg, 1.1 mmol, 69% yield). LCMS purity 95%: m/z 532 [M+H]+.

Stage 4: Cyclopentyl(2S)-4-{benzyl[4-(4,4,5,5-tetramethyl-1,3,2-dioxaborolan-2-yl)phenyl]amino}-2-[(tert-butoxycarbonyl)amino]butanoate To a mixture of cyclopentyl (2S)-4-[benzyl(4-bromophenyl)amino]-2-[(tert-butoxycarbonyl)amino]butanoate (0.55 g, 1.035 mmol), KOAc (0.152 g, 1.552 mmol), Bis[pinacolato]diboron (1.051 g, 4.14 mmol) and PdCl₂(dppf) (0.076 g, 0.103 mmol) was added DMSO. The suspension was purged with nitrogen and heated to 70° C. and monitored by LCMS for the formation of the product. After heating overnight, the reaction was poured on to a mixture of sat. NaHCO₃ and EtOAc, the layers separated and the aqueous layer extracted with EtOAc. The combined organic layers were washed with water (×2) and brine, then dried (MgSO₄), filtered and evaporated in vacuo. The dark residue was subjected to column chromatography eluting with 5 to 10% EtOAc in hexanes to give the product as a colourless oil (420 mg, 0.72 mmol, 70% yield). LCMS purity 95%: m/z 579 [M+H]+.

Intermediate 13
5-bromo-3-(carbamoylamino)thiophene-2-carboxamide

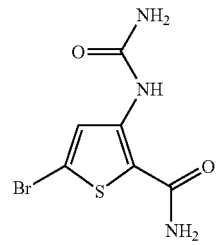

The synthesis of Intermediate 13 is detailed within WO2004063186.

EXAMPLES

The following examples illustrate the preparation of the specific compounds of the invention, and the IKK inhibitory properties thereof:

Example 1

Cyclopentyl O-{4-[4-carbamoyl-5-(carbamoylamino)-2-thienyl]phenyl}-D-homoserinate

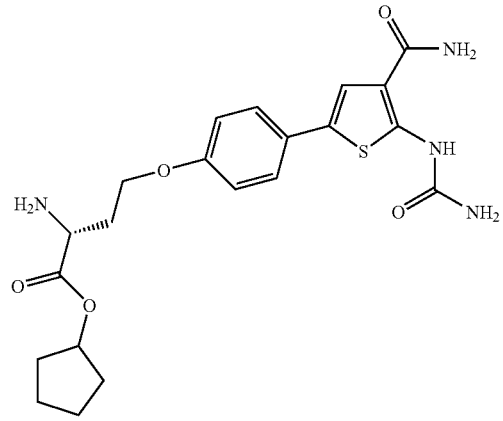

LC/MS purity 94%, m/z 447 [M+H]+, ¹H NMR (400 MHz, DMSO-d₆), δ: 10.9 (1H, s), 8.5 (3H, br s), 7.6 (1H, br s), 7.5 (1H, s), 7.4 (2H, d, J=8.8 Hz), 7.2 (1H, br s), 6.9 (2H, d, J=8.8 Hz), 5.1 (1H, m), 4.1 (3H, m), 2.2 (2H, m), 1.9-1.5 (8H, m).

The synthesis of Example 1 is shown in Scheme 1.

Stage 5—Cyclopentyl N-(tert-butoxycarbonyl)-O-{4-[4-carbamoyl-5-(carbamoylamino)-2-thienyl] phenyl}-D-homoserinate DME (6 ml) was added to a mixture of cyclopentyl N-(tert-butoxycarbonyl)-O-[4-(4,4,5,5-tetramethyl-1,3,2-dioxaborolan-2-yl)phenyl]-D-homoserinate (Intermediate 2a) (0.50 g, 1.022 mmol), Intermediate 1 (0.297 g, 1.124 mmol) and NaHCO₃ (0.681 ml, 2.043 mmol). The reaction was flushed thoroughly with nitrogen and tetrakis(triphenylphosphine) Pd catalyst (0.118 g, 0.102 mmol) added. The reaction was heated to 80° C. overnight. Reaction was cooled to room temperature and poured onto a mixture of DCM and sat NaHCO$_3$. The layers were separated and the aqueous layer extracted with 2×DCM (30 ml). The combined organic layers were dried over magnesium sulphate, filtered, absorbed onto silica and subjected to column chromatography eluting with 2% MeOH to 4% MeOH in DCM (198 mg, 36%). LCMS: m/z 548 [M+H]$^+$.

Stage 6—Cyclopentyl O-{4-[4-carbamoyl-5-(carbamoylamino)-2-thienyl]phenyl}-D-homoserinate A solution of Cyclopentyl N-(tert-butoxycarbonyl)-O-{4-[4-carbamoyl-5-(carbamoylamino)-2-thienyl]phenyl}-D-homoserinate (0.24 g, 0.439 mmol) in THF (2 ml) was cooled to 0° C. 4M HCl in dioxane (2.195 ml, 8.78 mmol) was added and the solution allowed to warm to room temperature with stirring. After 10 minutes, a further equivalent of HCl in dioxane (2.195 ml, 8.78 mmol) was added. The reaction was complete after 2 hours and the solvents were evaporated under reduced pressure and the residue triturated with THF (10 ml). The solid was collected, washed with a large volume of diethyl ether and dried under vacuum overnight (201 mg, 95%). LCMS: m/z 447 [M+H]$^+$.

The following examples were prepared in a similar manner to Example 1, using Intermediate 1 and the appropriate boronic ester, following the route shown in Scheme 1.

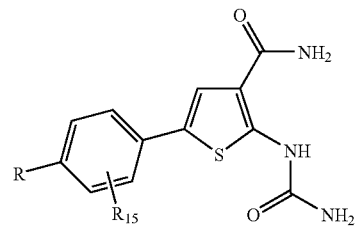

| Example Number | Intermediate used | R | R$_{15}$ | Name | LCMS purity |
|---|---|---|---|---|---|
| 2 | 2b | (structure) | H | Cyclopentyl O-{4-[4-carbamoyl-5-(carbamoylamino)-2-thienyl]phenyl}-L-homoserinate | 94% purity: m/z 447 [M + H]$^+$ |
| 3 | 3a | (structure) | H | Cyclopentyl 5-{4-[4-carbamoyl-5-(carbamoylamino)-2-thienyl]phenoxy}-L-norvalinate | 92% purity: m/z 461 [M + H]$^+$ |
| 4 | 3b | (structure) | H | Cyclopentyl 5-{4-[4-carbamoyl-5-(carbamoylamino)-2-thienyl]phenoxy}-D-norvalinate | 96% purity: m/z 461 [M + H]$^+$ |

-continued

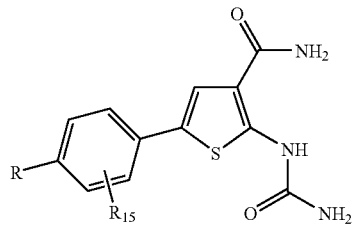

| Example Number | Intermediate used | R | R15 | Name | LCMS purity |
|---|---|---|---|---|---|
| 5 | 4a | ![structure] | 3-methyl | Cyclopentyl O-{4-[4-carbamoyl-5-(carbamoylamino)-2-thienyl]-3-methylphenyl}-L-homoserinate | 100% purity: m/z 461 [M + H]+ |
| 6 | 4b | ![structure] | 2-methyl | Cyclopentyl O-{4-[4-carbamoyl-5-(carbamoylamino)-2-thienyl]-2-methylphenyl}-L-homoserinate | 100% purity: m/z 461 [M + H]+ |
| 7 | 4c | ![structure] | 3-chloro | Cyclopentyl O-{4-[4-carbamoyl-5-(carbamoylamino)-2-thienyl]-3-chlorophenyl}-L-homoserinate | 100% purity: m/z 482 [M + H]+ |
| 8 | 4d | ![structure] | 2-chloro | Cyclopentyl O-{4-[4-carbamoyl-5-(carbamoylamino)-2-thienyl]-2-chlorolphenyl}-L-homoserinate | 98% purity: m/z 482 [M + H]+ |
| 9 | 5a | ![structure] | H | Cyclopentyl (2S,4E)-2-amino-5-{4-[4-carbamoyl-5-(carbamoylamino)-2-thienyl]phenyl}pent-4-enoate | 92% purity: m/z 443 [M + H]+ |

-continued

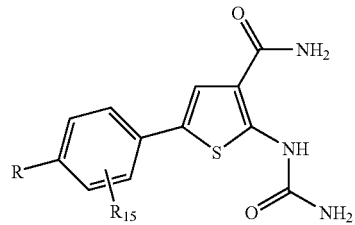

| Example Number | Intermediate used | R | R15 | Name | LCMS purity |
|---|---|---|---|---|---|
| 10 | 5b | (H2N, cyclopentyl ester, pent-4-enoate, 2R) | H | Cyclopentyl (2R,4E)-2-amino-5-{4-[4-carbamoyl-5-(carbamoylamino)-2-thienyl]phenyl}pent-4-enoate | 98% purity: m/z 443 [M + H]+ |
| 11 | 6a | (H2N, cyclopentyl ester, pentyl, L) | H | Cyclopentyl 5-{4-[4-carbamoyl-5-(carbamoylamino)-2-thienyl]phenyl}-L-norvalinate | 92% purity: m/z 445 [M + H]+ |
| 12 | 6b | (H2N, cyclopentyl ester, pentyl, D) | H | Cyclopentyl 5-{4-[4-carbamoyl-5-(carbamoylamino)-2-thienyl]phenyl}-D-norvalinate | 98% purity: m/z 445 [M + H]+ |
| 13 | 7a | (H2N, cyclopentyl ester, pent-4-enoate, 2S) | 3-chloro | Cyclopentyl (2S,4E)-2-amino-5-{4-[4-carbamoyl-5-(carbamoylamino)-2-thienyl]-3-chlorophenyl}pent-4-enoate | 99% purity: m/z 478 [M + H]+ |
| 14 | 7b | (H2N, cyclopentyl ester, pent-4-enoate, 2S) | 2-methyl | Cyclopentyl (2S,4E)-2-amino-5-{4-[4-carbamoyl-5-(carbamoylamino)-2-thienyl]-2-methylphenyl}pent-4-enoate | 100% purity: m/z 457 [M + H]+ |

-continued

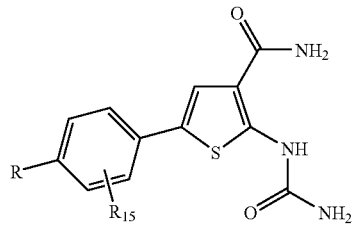

| Example Number | Intermediate used | R | R15 | Name | LCMS purity |
|---|---|---|---|---|---|
| 15 | 8 | (structure: H2N-CH(COO-cyclopentyl)-CH2-C≡C-C(CH3)3) | H | Cyclopentyl (2S)-2-amino-5-{4-[4-carbamoyl-5-(carbamoylamino)-2-thienyl]phenyl}pent-4-ynoate | 94% purity: m/z 441 [M + H]+ |
| 16 | 9 | (structure: H2N-CH(COO-cyclopentyl)-CH2-C(CH3)3) | H | Cyclopentyl 4-[4-carbamoyl-5-(carbamoylamino)-2-thienyl]-L-phenylalaninate | 99% purity: m/z 417 [M + H]+ |
| 17 | 10 | (structure: H2N-CH(COO-cyclopentyl)-CH2-CH2-O-CH2-C(CH3)3) | H | Cyclopentyl O-{4-[4-carbamoyl-5-(carbamoylamino)-2-thienyl]benzyl}-L-homoserinate | 98% purity: m/z 461 [M + H]+ |
| 18 | 11 | (structure: H2N-CH(COO-cyclopentyl)-CH2-CH=CH-C(CH3)3, Z) | H | Cyclopentyl (2S,4Z)-2-amino-5-{4-[4-carbamoyl-5-(carbamoylamino)-2-thienyl]phenyl}pent-4-enoate | 100% purity: m/z 443 [M + H]+ ~15% trans isomer by 1H NMR |
| 19* | Example 2 | (structure: cyclohexyl-NH-CH(COO-cyclopentyl)-CH2-CH2-O-C(CH3)3) | H | Cyclopentyl O-{4-[4-carbamoyl-5-(carbamoylamino)thiophen-2-yl]phenyl}-N-cyclohexyl-L-homoserinate | 95% purity: m/z 529 [M + H]+ |

-continued

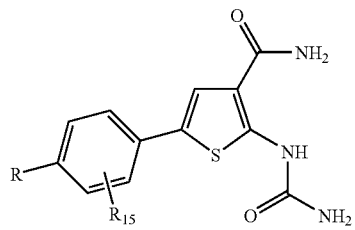

| Example Number | Intermediate used | R | R15 | Name | LCMS purity |
|---|---|---|---|---|---|
| 20** | Example 10 | (cyclohexyl-NH-CH(CH=CH-C(CH3)3)-CH2-C(=O)-O-cyclopentyl) | H | Cyclopentyl (2R,4E)-5-{4-[4-carbamoyl-5-(carbamoylamino)thiophen-2-yl]phenyl}-2-(cyclohexylamino)pent-4-enoate | 100% purity: m/z 525 [M + H]+ |
| 21 | 12 | (H2N-CH(CH2-N(Bn)(tBu))-C(=O)-O-cyclopentyl) | H | Cyclopentyl (2S)-2-amino-4-(benzyl{4-[4-carbamoyl-5-(carbamoylamino)thiophen-2-yl]phenyl}amino)butanoate | 91% purity: m/z 536 [M + H]+ |
| 22 | 5c | (H2N-CH(CH2-CH=CH-C(CH3)3)-C(=O)-O-tBu) | H | tert-Butyl (2S,4E)-2-amino-5-{4-[4-carbamoyl-5-(carbamoylamino)-2-thienyl]phenyl}pent-4-enoate | 97% purity: m/z 431 [M + H]+ |

*The synthesis of Example 19 is shown in Scheme 9 and detailed experimental is shown below.

Stage 1: Cyclopentyl O-{4-[4-carbamoyl-5-(carbamoylamino)thiophen-2-yl]phenyl}-N-cyclohexyl-L-homoserinate Cyclohexanone (50.4 mg, 514 μmol) was added to a solution of Example 2 (153 mg, 343 μmol) in THF (5 ml) and stirred at RT for 30 minutes. Sodium triacetoxyborohydride (363 mg, 1713 μmol) was then added slowly. After stirring at RT for 1 hr, LCMS indicated good conversion to the product. The reaction mixture was poured onto 0.5M HCl (5 ml) and DCM (10 ml) and allowed to stir 10 minutes. The mixture was then poured on to a large volume of sat. NaHCO3, the layers separated and the aqueous layer extracted with two further portions of DCM. The combined organics extracts were dried over MgSO4, filtered and evaporated in vacuo to give a brown oil (~300 mg). The crude product was purified by column chromatography eluting with 5% MeOH in DCM to give the product as a white solid (65 mg, 123 μmol, 36%).

**The synthesis of Example 20 follows analogous experimental details to Example 19.

The following examples were prepared in a similar manner to Example 1, using Intermediate 13.

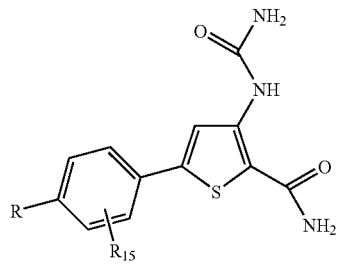

| Example Number | Intermediate used | R | R$_{15}$ | Name | LCMS purity |
|---|---|---|---|---|---|
| 23 | 13 and 2b | ![structure] | H | Cyclopentyl O-{4-[5-carbamoyl-4-(carbamoylamino)-2-thienyl]phenyl}-L-homoserinate | 95% purity: m/z 447 [M + H]$^+$ |
| 24 | 13 and 9 | ![structure] | H | Cyclopentyl 4-[5-carbamoyl-4-(carbamoylamino)-2-thienyl]-L-phenylalaninate | 98% purity: m/z 417 [M + H]$^+$ |

NMR Data

| Example Number | NMR assignment |
|---|---|
| 1 | $^1$H NMR (400 MHz, DMSO-d$_6$), δ: 10.9 (1H, s), 8.5 (3H, br s), 7.6 (1H, br s), 7.5 (1H, s), 7.4 (2H, d, J = 8.8 Hz), 7.2 (1H, br s), 6.9 (2H, d, J = 8.8 Hz), 5.1 (1H, m), 4.1 (3H, m), 2.2 (2H, m), 1.9-1.5 (8H, m). |
| 5 | $^1$H NMR (400 MHz, DMSO- d$_6$), δ: 10.94 (1H, s), 7.63 (1H, br. s), 7.16-7.26 (2H, m), 6.81 (1H, br. s), 6.74 (2H, d, J = 8.6 Hz), 5.05 (1H, t, J = 6.1 Hz), 4.04 (3H, m), 3.27 (3H, s), 1.78 (2H, m), 1.49-1.61 (8H, m). |
| 7 | $^1$H NMR (400 MHz, DMSO- d$_6$) δ: 10.97 (1H, s), 7.66 (1H, br s), 7.45 (1H, s), 7.41 (1H, d, J = 8.8 Hz), 7.22 (1H, br s), 7.06 (1H, d, J = 2.4 Hz), 6.93 (H, dd, J = 8.8 Hz), 6.90 (1H, br s), 5.05 (1H, m), 4.03-4.15 (3H, m), 1.91-2.03 (1H, m), 1.78 (2H, m), 1.48-1.60 (5H, m). |
| 9 | $^1$H NMR (400 MHz, DMSO- d$_6$), δ: 10.96 (1H, s), 7.67 (1H, br s), 7.38-7.49 (2H, d, J = 8.8 Hz), 7.32-7.38 (2H, d, J = 8.8 Hz), 7.25 (1H, br s), 6.94 (1H, br. s), 6.33-6.40 (2H, m), 5.03 (1H, t, J = 5.9 Hz), 3.38 (1H, t, J = 6.4 Hz), 2.33-2.44 (2H, m), 1.85-1.65 (2H, m), 1.40-1.60 (6H, m). |
| 10 | $^1$H NMR (400 MHz, DMSO- d$_6$), δ: 11.0 (1H, s), 7.7 (1H, s), 7.6 (1H, br s), 7.4 (2H, d, J = 8.4 Hz), 7.3 (2H, d, J = 8.4 Hz), 7.3 (1H, br s), 6.9 (2H, br s), 6.4 (1H, d, J = 15.4 Hz), 6.2 (1H, m), 5.0 (1H, m), 3.4 (1H, t, J = 6.2 Hz), 2.4 (2H, m), 2.1 (2H, br s), 1.7 (2H, m), 1.6-1.4 (6H, m). |
| 11 | $^1$H NMR (400 MHz, DMSO- d$_6$), δ: 10.94 (1H, s), 7.63 (2H, s), 7.39 (2H, d, J = 8.3 Hz), 7.25 (1H, br. s), 7.15 (2H, d, J = 8.3 Hz), 6.91 (1H, br. s), 5.02 (1 H, br. s), 5.02 (1H, t, J = 5.9 Hz), 3.23 (3H, m), 2.48-2.58 (2H, m), 1.75 (2H, m), 1.50-1.65 (8H, m). |
| 12 | $^1$H NMR (400 MHz, DMSO- d$_6$), δ: 10.9 (1H, s), 7.6 (2H, br s), 7.4 (2H, d, J = 8.0 Hz), 7.3 (1H, br s), 7.2 (2H, d, J = 8.0 Hz), 6.9 (2H, br s), 5.0 (1H, m), 3.2 (1H, m), 2.5 (2H, m), 1.8 (5H, m), 1.7-1.6 (2H, m), 1.6-1.5 (8H, m). |

-continued

| Example Number | NMR assignment |
|---|---|
| 13 | $^1$H NMR (400 MHz, DMSO-$d_6$), δ: 11.0 (1H, s), 7.8 (1H, br s), 7.7 (1H, s), 7.5 (2H, m), 7.4 (1H, m), 7.3 (1H, br s), 7.0 (2H, br s), 6.4 (2H, m), 5.1 (1H, m), 3.4 (1H, t, J = 6.4 Hz), 2.4 (2H, m), 1.9-1.7 (4H, m), 1.7-1.4 (6H, m). |
| 14 | $^1$H NMR (400 MHz, DMSO-$d_6$), δ: 11.0 (1H, s), 7.7 (1H, s), 7.7 (1H, br s), 7.5 (1H, d, J = 8 Hz), 7.3 (3H, m), 6.9 (2H, br s), 6.6 (1H, d, J = 16.0 Hz), 6.1 (1H, m), 5.1 (1H, m), 3.4 (1H, t, J = 6.2 Hz), 2.5 (2H, m), 2.3 (3H, s), 1.9-1.7 (4H, m), 1.7-1.4 (6H, m). |
| 16 | $^1$H NMR (400 MHz, DMSO-$d_6$), δ: 10.95 (1H, s), 7.64 (2H, s), 7.38 (2H, d, J = 8.3 Hz), 7.25 (1H, br. s), 7.16 (2H, d, J = 8.3 Hz), 6.91 (1H, br. s), 4.97 (1 H, br. s), 4.96 (1H, t, J = 6.1 Hz), 3.46-3.51 (1H, m), 2.75 (2H, d, J = 6.8 Hz), 1.75 (2H, m), 1.50-1.65 (8H, m). |

Example 25

O-{4-[4-Carbamoyl-5-(carbamoylamino)-2-thienyl]phenyl}-D-homoserine

LC/MS purity 94%, m/z 379 [M+H]$^+$, $^1$H NMR (400 MHz, DMSO-$d_6$), δ: 10.9 (1H, s), 8.5 (3H, br s), 7.6 (1H, br s), 7.5 (1H, s), 7.29 (2H, d, J=8.8 Hz), 7.2 (1H, br s), 6.9 (2H, d, J=8.8 Hz), 4.1 (3H, m), 2.2 (2H, m).

The synthetic route to Example 25 is detailed in Scheme 1 using Example 1.

Stage 7

To a solution of Cyclopentyl O-{4-[4-carbamoyl-5-(carbamoylamino)-2-thienyl]phenyl}-D-homoserinate (Example 1) (0.05 g, 0.104 mmol) in THF was added lithium hydroxide (25 mg, 1.035 mmol) in 1 ml water. The solution was allowed to stir at room temperature and monitored by LCMS for the formation of the product. After 2 hrs the reaction was judged to be complete. The THF was evaporated under vacuum and the aqueous diluted with further water (2 ml). Acetic acid was added dropwise until the pH was acidic (~10 drops), the precipitate formed was collected via filtration and washed with water (3 ml), ethanol (5 ml) and diethyl ether (10 ml). The product was isolated as an off-white solid (29 mg, 74%).

The following examples were prepared in a similar manner to Example 25.

| Example Number | Example used | R | $R_{15}$ | Name | LCMS purity |
|---|---|---|---|---|---|
| 26 | 2 | 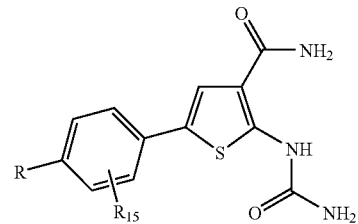 | H | O-{4-[4-carbamoyl-5-(carbamoylamino)-2-thienyl]phenyl}-L-homoserine | 94% purity: m/z 447 [M + H]$^+$ |

-continued

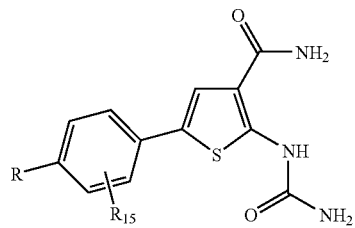

| Example Number | Example used | R | R15 | Name | LCMS purity |
|---|---|---|---|---|---|
| 27 | 3 | (O-tBu norvaline, H2N, COOH) | H | 5-{4-[4-carbamoyl-5-(carbamoylamino)-2-thienyl]phenoxy}-L-norvaline | 96% purity: m/z 393 [M + H]+ |
| 28 | 4 | (O-tBu norvaline, D) | H | 5-{4-[4-carbamoyl-5-(carbamoylamino)-2-thienyl]phenoxy}-D-norvaline | 93% purity: m/z 393 [M + H]+ |
| 29 | 5 | (O-tBu homoserine, L) | 3-methyl | O-{4-[4-carbamoyl-5-(carbamoylamino)-2-thienyl]-3-methylphenyl}-L-homoserine | 100% purity: m/z 393 [M + H]+ |
| 30 | 6 | (O-tBu homoserine, L) | 2-methyl | O-{4-[4-carbamoyl-5-(carbamoylamino)-2-thienyl]-2-methylphenyl}-L-homoserine | 100% purity: m/z 393 [M + H]+ |
| 31 | 7 | (O-tBu homoserine, L) | 3-chloro | O-{4-[4-carbamoyl-5-(carbamoylamino)-2-thienyl]-3-chlorophenyl}-L-homoserine | 100% purity: m/z 414 [M + H]+ |

-continued

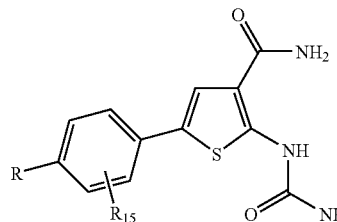

| Example Number | Example used | R | R15 | Name | LCMS purity |
|---|---|---|---|---|---|
| 32 | 8 | (H2N-CH(COOH)-CH2-CH2-O-C(CH3)3) | 2-chloro | O-{4-[4-carbamoyl-5-(carbamoylamino)-2-thienyl]-2-chlorophenyl}-L-homoserine | 100% purity: m/z 414 [M + H]+ |
| 33 | 9 | (H2N-CH(COOH)-CH2-CH=CH-C(CH3)3, 2S,4E) | H | (2S,4E)-2-amino-5-{4-[4-carbamoyl-5-(carbamoylamino)-2-thienyl]phenyl}pent-4-enoic acid | 98% purity: m/z 375 [M + H]+ |
| 34 | 10 | (H2N-CH(COOH)-CH2-CH=CH-C(CH3)3, 2R,4E) | H | (2R,4E)-2-amino-5-{4-[4-carbamoyl-5-(carbamoylamino)-2-thienyl]phenyl}pent-4-enoic acid | 100% purity: m/z 375 [M + H]+ |
| 35 | 11 | (L-norvaline-tBu derivative) | H | 5-{4-[4-carbamoyl-5-(carbamoylamino)-2-thienyl]phenyl}-L-norvaline | 98% purity: m/z 377 [M + H]+ |
| 36 | 12 | (D-norvaline-tBu derivative) | H | 5-{4-[4-carbamoyl-5-(carbamoylamino)-2-thienyl]phenyl}-D-norvaline | 99% purity: m/z 377 [M + H]+ |

-continued

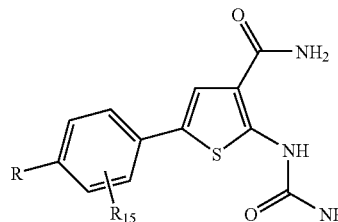

| Example Number | Example used | R | $R_{15}$ | Name | LCMS purity |
|---|---|---|---|---|---|
| 37 | 13 | (4E)-6,6-dimethyl-2-amino-hept-4-enoic acid side chain | 3-chloro | (2S,4E)-2-amino-5-{4-[4-carbamoyl-5-(carbamoylamino)-2-thienyl]-3-chlorophenyl}pent-4-enoic acid | 99% purity: m/z 410 [M + H]$^+$ |
| 38 | 14 | (4E)-6,6-dimethyl-2-amino-hept-4-enoic acid side chain | 2-methyl | (2S,4E)-2-amino-5-{4-[4-carbamoyl-5-(carbamoylamino)-2-thienyl]-2-methylphenyl}pent-4-enoic acid | 100% purity: m/z 389 [M + H]$^+$ |
| 39 | 15 | 6,6-dimethyl-2-amino-hept-4-ynoic acid side chain | H | (2S)-2-amino-5-{4-[4-carbamoyl-5-(carbamoylamino)-2-thienyl]phenyl}pent-4-ynoic acid | 95% purity: m/z 373 [M + H]$^+$ |
| 40 | 16 | tert-butyl phenylalanine side chain | H | 4-[4-carbamoyl-5-(carbamoylamino)-2-thienyl]-L-phenylalanine | 97% purity: m/z 349 [M + H]$^+$ |
| 41 | 17 | O-neopentyl homoserine side chain | H | O-{4-[4-carbamoyl-5-(carbamoylamino)-2-thienyl]benzyl}-L-homoserine | 97% purity: m/z 393 [M + H]$^+$ |

-continued

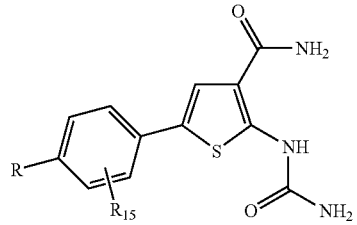

| Example Number | Example used | R | R15 | Name | LCMS purity |
|---|---|---|---|---|---|
| 42 | 18 | (H2N, COOH, pentenyl with tBu) | H | (2S,4Z)-2-amino-5-{4-[4-carbamoyl-5-(carbamoylamino)-2-thienyl]phenyl}pent-4-enoic acid | 100% purity: m/z 375 [M + H]+ ~25% trans isomer by 1H NMR |
| 43 | 19 | (cyclohexyl-NH, COOH, O-tBu homoserine) | H | O-{4-[4-carbamoyl-5-(carbamoylamino)thiophen-2-yl]phenyl}-N-cyclohexyl-L-homoserine | 95% purity: m/z 461 [M + H]+ |
| 44 | 20 | (cyclohexyl-NH, COOH, pentenyl tBu) | H | (2R,4E)-5-{4-[4-carbamoyl-5-(carbamoylamino)thiophen-2-yl]phenyl}-2-(cyclohexylamino)pent-4-enoic acid | 100% purity: m/z 457 [M + H]+ |
| 45 | 21 | (H2N, COOH, benzyl-N-tBu butanoic) | H | (2S)-2-amino-4-(benzyl{4-[4-carbamoyl-5-(carbamoylamino)thiophen-2-yl]phenyl}amino)butanoic acid | 92% purity: m/z 468 [M + H]+ |

The following examples were prepared in a similar manner to Example 25.

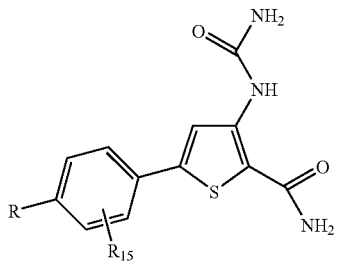

| Example Number | Example used | R | R$_{15}$ | Name | LCMS purity |
|---|---|---|---|---|---|
| 46 | 23 | ![structure with H$_2$N, O, OH homoserine derivative] | H | O-{4-[5-carbamoyl-4-(carbamoylamino)-2-thienyl]phenyl}-L-homoserine | 92% purity: m/z 379 [M + H]$^+$ |
| 47 | 24 | ![structure with H$_2$N, O, OH tert-butyl derivative] | H | 4-[5-carbamoyl-4-(carbamoylamino)2-thienyl]-L-phenylalanine | 98% purity: m/z 349 [M + H]$^+$ |

Measurement of Biological Activity

IKKβ Enzyme Assay

The ability of compounds to inhibit IKKβ kinase activity was measured in an assay performed by Invitrogen (Paisley, UK). The Z'-LYTE™ biochemical assay employs a fluorescence-based, coupled-enzyme format and is based on the differential sensitivity of phosphorylated and non-phosphorylated peptides to proteolytic cleavage. The peptide substrate is labelled with two fluorophores—one at each end—that make up a FRET pair. In the primary reaction, the kinase transfers the gamma-phosphate of ATP to a single serine or threonine residue in a synthetic FRET-peptide. In the secondary reaction, a site-specific protease recognizes and cleaves non-phosphorylated FRET-peptides. Phosphorylation of FRET-peptides suppresses cleavage by the Development Reagent. Cleavage disrupts FRET between the donor (i.e., coumarin) and acceptor (i.e. fluorescein) fluorophores on the FRET-peptide, whereas uncleaved, phosphorylated FRET-peptides maintain FRET. A radiometric method, which calculates the ratio (the Emission Ratio) of donor emission to acceptor emission after excitation of the donor fluorophore at 400 nm, is used to quantitate reaction progress.

The final 10 μL Kinase Reaction consists of 0.9-8.0 ng IKBKB (IKKβ), 2 μM Ser/Thr 05 Peptide and ATP in 50 mM HEPES pH 7.5, 0.01% BRIJ-35, 10 mM MgCl$_2$, 1 mM EGTA. The assay is performed at an ATP concentration at, or close to the Km. After the 60 minute Kinase Reaction incubation at room temperature, 5 μL of a 1:128 dilution of Development Reagent is added. The assay plate is incubated for a further 60 minutes at room temperature and read on a fluorescence plate reader.

Duplicate data points are generated from a ⅓ log dilution series of a stock solution of test compound in DMSO. Nine dilutions steps are made from a top concentration of 10 μM, and a 'no compound' blank is included. Data is collected and analysed using XLfit software from IDBS. The dose response curve is curve fitted to model number 205 (sigmoidal dose-response model). From the curve generated, the concentration giving 50% inhibition is determined and reported.

LPS-Stimulation of THP-1 Cells

THP-1 cells were plated in 100 μl at a density of 4×10$^4$ cells/well in V-bottomed 96 well tissue culture treated plates and incubated at 37° C. in 5% CO$_2$ for 16 hrs. 2 hrs after the addition of the inhibitor in 100 μl of tissue culture media, the cells were stimulated with LPS (*E coli* strain 005:B5, Sigma) at a final concentration of 1 μg/ml and incubated at 37° C. in 5% $CO_2$ for 6 hrs. TNF-α levels were measured from cell-free supernatants by sandwich ELISA (R&D Systems #QTA00B)

LPS-Stimulation of Human Whole Blood

Whole blood was taken by venous puncture using heparinised vacutainers (Becton Dickinson) and diluted in an equal volume of RPMI1640 tissue culture media (Sigma). 100 μl was plated in V-bottomed 96 well tissue culture treated plates. 2 hrs after the addition of the inhibitor in 100 μl of RPMI1640 media, the blood was stimulated with LPS (*E coli* strain 005:B5, Sigma) at a final concentration of 100 ng/ml and incubated at 37° C. in 5% $CO_2$ for 6 hrs. TNF-α levels were measured from cell-free supernatants by sandwich ELISA (R&D Systems #QTA00B)

IC50 values were allocated to one of three ranges as follows:

Range A: IC50<1000 nM
Range B: 1000 nM<IC50<5000 nM
Range C: IC50>5000 nM
NT=not tested Results Table

| Example Number | Inhibitor activity versus IKKβ | Inhibitor activity versus THP-1 TNFα release | Inhibitor activity versus human whole blood TNFα release |
|---|---|---|---|
| 1 | A | A | B |
| 2 | A | B | NT |
| 3 | A | B | C |
| 4 | A | B | NT |
| 5 | A | A | C |
| 6 | A | A | C |
| 7 | A | A | C |
| 8 | A | B | C |
| 9 | A | A | A |
| 10 | A | A | A |
| 11 | A | A | B |
| 12 | A | A | NT |
| 13 | A | A | B |
| 14 | A | A | A |
| 15 | A | B | C |
| 16 | A | A | B |
| 17 | A | B | NT |
| 18 | A | B | B |
| 19 | A | C | NT |
| 20 | A | B | NT |
| 21 | A | B | NT |
| 22 | NT | NT | NT |
| 23 | A | B | NT |
| 24 | A | C | NT |
| 25 | A | NT | NT |
| 26 | A | NT | NT |
| 27 | A | NT | NT |
| 28 | A | NT | NT |
| 29 | A | NT | NT |
| 30 | A | NT | NT |
| 31 | A | NT | NT |
| 32 | A | NT | NT |
| 33 | A | NT | NT |
| 34 | A | NT | NT |
| 35 | A | NT | NT |
| 36 | A | NT | NT |
| 37 | A | NT | NT |
| 38 | A | NT | NT |
| 39 | A | NT | NT |
| 40 | A | NT | NT |
| 41 | A | NT | NT |
| 42 | A | NT | NT |
| 43 | A | NT | NT |
| 44 | A | NT | NT |
| 45 | A | NT | NT |
| 46 | A | NT | NT |
| 47 | A | NT | NT |

Broken Cell Carboxylesterase Assay

Any given compound of the present invention wherein $R_1$ is an ester group, may be tested to determine whether it meets the requirement that it be hydrolysed by intracellular esterases, by testing in the following assay.

Preparation of Cell Extract

U937 or HCT 116 tumour cells (~$10^9$) were washed in 4 volumes of Dulbeccos PBS (~1 liter) and pelleted at 525 g for 10 min at 4° C. This was repeated twice and the final cell pellet was resuspended in 35 ml of cold homogenising buffer (Trizma 10 mM, NaCl 130 mM, $CaCl_2$ 0.5 mM pH 7.0 at 25° C.). Homogenates were prepared by nitrogen cavitation (700 psi for 50 min at 4° C.). The homogenate was kept on ice and supplemented with a cocktail of inhibitors at final concentrations of:

Leupeptin 1 μM

Aprotinin 0.1 μM

E64 8 μM

Pepstatin 1.5 μM

Bestatin 162 μM

Chymostatin 33 μM

After clarification of the cell homogenate by centrifugation at 525 g for 10 min, the resulting supernatant was used as a source of esterase activity and was stored at −80° C. until required.

Measurement of Ester Cleavage

Hydrolysis of esters to the corresponding carboxylic acids can be measured using the cell extract, prepared as above. To this effect cell extract (~30 μg/total assay volume of 0.5 ml) was incubated at 37° C. in a Tris-HCl 25 mM, 125 mM NaCl buffer, pH 7.5 at 25° C. At zero time the ester (substrate) was then added at a final concentration of 2.5 μM and the samples were incubated at 37° C. for the appropriate time (usually 0 or 80 min). Reactions were stopped by the addition of 3× volumes of acetonitrile. For zero time samples the acetonitrile was added prior to the ester compound. After centrifugation at 12000 g for 5 min, samples were analysed for the ester and its corresponding carboxylic acid at room temperature by LCMS (Sciex API 3000, HP1100 binary pump, CTC PAL). Chromatography was based on an AcCN (75×2.1 mm) column and a mobile phase of 5-95% acetonitrile in water/0.1% formic acid.

Table 1 presents data showing that several amino acid ester motifs, conjugated to various intracellular enzyme inhibitors by several different linker chemistries are all hydrolysed by intracellular carboxyesterases to the corresponding acid.

TABLE 1
| Structure of amino acid ester conjugate | R | Linker | Hydrolysis Rate Range U937Cells (pg/mL/min) | Preparation of amino ester conjugate |
|---|---|---|---|---|
| 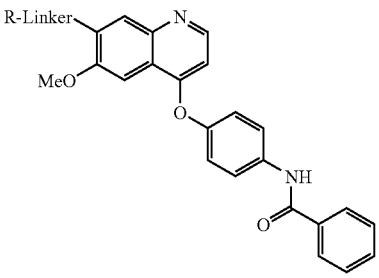 | 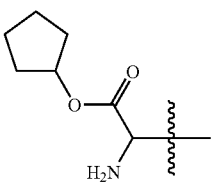 | ~CH2CH2O~ | 100-1000 | WO2006117552 |
| 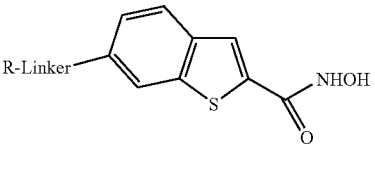 | 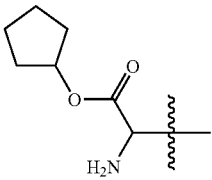 | 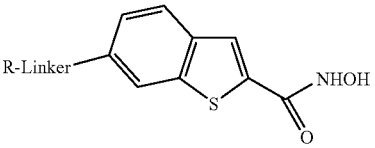 (CH₂)₃O—⌬—CH₂NHCH₂ | 1000-50000 | WO2006117548 |
| 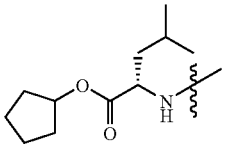 | 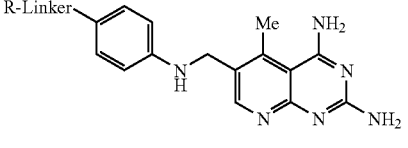 | CH₂—⌬—CH₂NHCH₂ | >50000 | WO2006117549 |
| 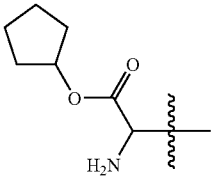 | 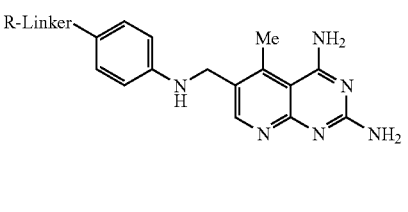 | ~CH2CH2O~ | >50000 | WO2006117567 |
| 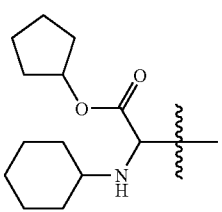 | 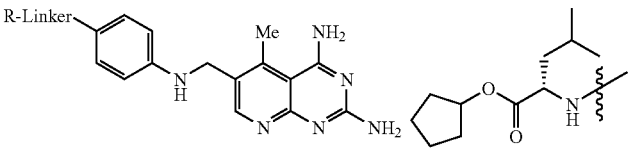 | ~CH2CH2O~ | 1000-50000 | WO2006117567 |
| 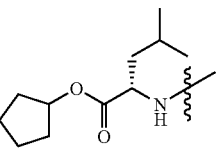 | 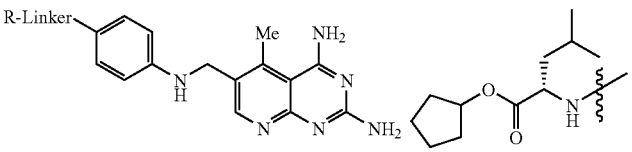 | ~CH2~ | 1000-50000 | WO2006117567 |
| 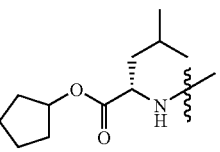 | | ~CO~ | >50000 | WO2006117567 |

TABLE 1-continued

| Structure of amino acid ester conjugate | R | Linker | Hydrolysis Rate Range U937Cells (pg/mL/min) | Preparation of amino ester conjugate |
|---|---|---|---|---|
| 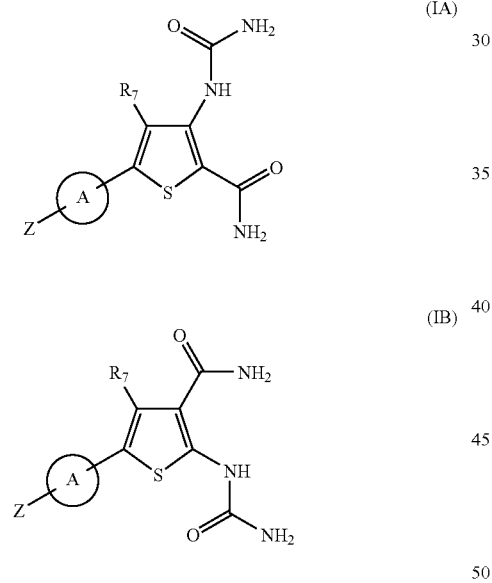 | | ~CH$_2$-⟨phenyl⟩-CH$_2$NHCH$_2$~ 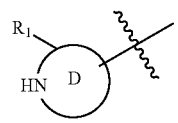 | >50000 | WO2006117549 |
| | | ~CH$_2$-⟨phenyl⟩-CH$_2$NHCH$_2$~ | >50000 | WO2006117549 |

The invention claimed is:

1. A compound of formula (IA) or (IB), or a salt, N-oxide, hydrate or solvate thereof:

(IA)

(IB)

wherein

R$_7$ is hydrogen or optionally substituted (C$_1$-C$_6$)alkyl;

ring A is an optionally substituted aryl or heteroaryl ring of 5-13 ring atoms;

Z is a radical of formula R-L$^1$-Y$^1$—(CH$_2$)$_z$—, wherein:

R is a radical of formula (X) or (Y)

(X)

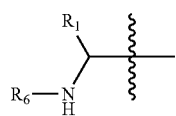

(Y)

R$_1$ is a carboxylic acid group (—COOH), or an ester group which is hydrolysable by one or more intracellular esterase enzymes to a carboxylic acid group;

R$_6$ is hydrogen; or optionally substituted C$_1$-C$_6$ alkyl, C$_3$-C$_7$ cycloalkyl, aryl or heteroaryl or —(C═O)R$_3$, —(C═O)OR$_3$, or —(C═O)NR$_3$ wherein R$_3$ is hydrogen or optionally substituted (C$_1$-C$_6$)alkyl, Y$^1$ is a bond, —(C═O)—, —S(O$_2$)—, —C(═O)O—, —OC(═O)—, —(C═O)NR$_3$—, —NR$_3$(C═O)—, —S(O$_2$)NR$_3$—, —NR$_3$S(O$_2$)—, or —NR$_3$(C═O)NR$_4$—, wherein R$_3$ and R$_4$ are independently hydrogen or optionally substituted (C$_1$-C$_6$)alkyl, L$^1$ is a divalent radical of formula -(Alk$^1$)$_m$(Q)$_n$(Alk$^2$)$_p$- wherein m, n and p are independently 0 or 1, Q is (i) an optionally substituted divalent mono- or bicyclic carbocyclic or heterocyclic radical having 5-13 ring members, or (ii), in the case where p is 0, a divalent radical of formula -Q$^1$-X$^2$- wherein X$^2$ is —O—, —S— or NR$^A$— wherein R$^A$ is hydrogen or optionally substituted C$_1$-C$_3$ alkyl, and Q$^1$ is an optionally substituted divalent mono- or bicyclic carbocyclic or heterocyclic radical having 5-13 ring members, Alk$^1$ and Alk$^2$ independently represent optionally substituted divalent C$_3$-C$_7$ cycloalkyl radicals, or optionally substituted straight or branched, C$_1$-C$_6$ alkylene, C$_2$-C$_6$ alkenylene, or C$_2$-C$_6$ alkynylene radicals which may optionally contain or terminate in an ether (—O—), thioether (—S—) or amino (—NR$^A$—) link wherein R$^A$ is hydrogen or optionally substituted C$_1$-C$_3$ alkyl; and z is 0 or 1.

2. A compound as claimed in claim 1 wherein R$_7$ is hydrogen.

3. A compound as claimed in claim 1 wherein ring A is optionally substituted 1,4-phenylene or 1,3-phenylene.

4. A compound as claimed in claim 1 any of the preceding claims wherein optional substituents in ring A are selected from, fluoro, chloro, methyl, and trifluoromethyl.

5. A compound as claimed in claim 1 wherein $R_1$ is an ester group of formula —(C=O)O$R_{14}$ wherein $R_{14}$ is $R_8R_9R_{10}$C— wherein
  (i) $R_8$ is hydrogen or optionally substituted $(C_1-C_3)$alkyl-$(Z^1)_a$—[$(C_1-C_3)$alkyl]$_b$- or $(C_2-C_3)$alkenyl-$(Z^1)_a$—[$(C_1-C_3)$alkyl]$_b$- wherein a and b are independently 0 or 1 and $Z^1$ is —O—, —S—, or —N$R_{11}$— wherein $R_{11}$ is hydrogen or $(C_1-C_3)$alkyl; and $R_9$ and $R_{10}$ are independently hydrogen or $(C_1-C_3)$alkyl-;
  (ii) $R_8$ is hydrogen or optionally substituted $R_{12}R_{13}$N—$(C_1-C_3)$alkyl- wherein $R_{12}$ is hydrogen or $(C_1-C_3)$alkyl and $R_{13}$ is hydrogen or $(C_1-C_3)$alkyl; or $R_{12}$ and $R_{13}$ together with the nitrogen to which they are attached form an optionally substituted monocyclic heterocyclic ring of 5- or 6-ring atoms or bicyclic heterocyclic ring system of 8 to 10 ring atoms, and $R_9$ and $R_{10}$ are independently hydrogen or $(C_1-C_3)$alkyl-; or
  (iii) $R_8$ and $R_9$ taken together with the carbon to which they are attached form an optionally substituted monocyclic carbocyclic ring of from 3 to 7 ring atoms or bicyclic carbocyclic ring system of 8 to 10 ring atoms, and $R_{10}$ is hydrogen.

6. A compound as claimed in claim 1 wherein $R_1$ is a methyl, ethyl, n- or iso-propyl, n-, sec- or tert-butyl, cyclohexyl, allyl, phenyl, benzyl, 2-, 3- or 4-pyridylmethyl, N-methylpiperidin-4-yl, tetrahydrofuran-3-yl, methoxyethyl, indanyl, norbornyl, dimethylaminoethyl, or morpholinoethyl ester group.

7. A compound as claimed in claim 1 wherein $R_1$ is a cyclopentyl or tert-butyl ester.

8. A compound as claimed in claim 1 wherein $R_6$ is hydrogen.

9. A compound as claimed in claim 1 wherein
-L$^1$-Y$^1$—(CH$_2$)$_z$— in Z is —(CH$_2$)$_a$(O)$_d$(CH$_2$)$_a$ wherein a is 1, 2 or 3, b is 0, 1 or 2, and d is 0 or 1, —CH=CH—, —CH$_2$CH=CH—, —CH=CHCH$_2$—, —C≡C—, —CH$_2$C≡C—, or —C≡CCH$_2$—.

10. A compound as claimed in claim 1 selected from the group consisting of
Cyclopentyl O-{4-[4-carbamoyl-5-(carbamoylamino)-2-thienyl]phenyl}-D-homoserinate,
Cyclopentyl O-{4-[4-carbamoyl-5-(carbamoylamino)-2-thienyl]-3-methylphenyl}-L-homoserinate,
Cyclopentyl O-{4-[4-carbamoyl-5-(carbamoylamino)-2-thienyl]-3-chlorophenyl}-L-homoserinate,
Cyclopentyl(2S,4E)-2-amino-5-{4-[4-carbamoyl-5-(carbamoylamino)-2-thienyl]phenyl}pent-4-enoate,
Cyclopentyl(2R,4E)-2-amino-5-{4-[4-carbamoyl-5-(carbamoylamino)-2-thienyl]phenyl}pent-4-enoate,
Cyclopentyl 5-{4-[4-carbamoyl-5-(carbamoylamino)-2-thienyl]phenyl}-L-norvalinate,
Cyclopentyl 5-{4-[4-carbamoyl-5-(carbamoylamino)-2-thienyl]phenyl}-D-norvalinate,
Cyclopentyl(2S,4E)-2-amino-5-{4-[4-carbamoyl-5-(carbamoylamino)-2-thienyl]-3-chlorophenyl}pent-4-enoate,
Cyclopentyl(2S,4E)-2-amino-5-{4-[4-carbamoyl-5-(carbamoylamino)-2-thienyl]-2-methylphenyl}pent-4-enoate, and
Cyclopentyl 4-[4-carbamoyl-5-(carbamoylamino)-2-thienyl]-L-phenylalaninate,
and salts, N-oxides, hydrates or solvates thereof.

11. A pharmaceutical composition comprising a compound as claimed in claim 1 together with one or more pharmaceutically acceptable carriers and/or excipients.

12. A method for the treatment of neoplastic/proliferative, immune or inflammatory disease, which comprises administering to a subject suffering such disease an effective amount of a compound as claimed in claim 1.

13. The method as claimed in claim 12 for the treatment of hepatocellular cancer or melanoma.

14. The method as claimed in claim 12 for the treatment of bowel cancer, ovarian cancer, head and neck and cervical squamous cancers, gastric or lung cancers, anaplastic oligodendrogliomas, glioblastoma multiforme or medulloblastomas.

15. The method as claimed in claim 12 for the treatment of rheumatoid arthritis, psoriasis, inflammatory bowel disease, Crohn's disease, ulcerative colitis, chronic obstructive pulmonary disease, asthma, multiple sclerosis, diabetes, atopic dermatitis, graft versus host disease, or systemic lupus erythematosus.

* * * * *